United States Patent
Ferro et al.

[11] Patent Number: 6,083,969
[45] Date of Patent: Jul. 4, 2000

[54] 1,3- AND 2,3-DIARYLCYCLOALKANO AND CYCLOALKENO PYRAZOLES AS SELECTIVE INHIBITORS OF CYCLOOXYGENASE-2 AND ANTIINFLAMMATORY AGENTS

[75] Inventors: Michael Ferro, Bridgewater; Zhihua Sui, Flemington; Michael Wachter, Bloomsbury, all of N.J.

[73] Assignee: Ortho-McNeil Pharaceutical, Inc., Raritan, N.J.

[21] Appl. No.: 09/421,999

[22] Filed: Oct. 20, 1999

Related U.S. Application Data
[60] Provisional application No. 60/106,149, Oct. 29, 1998.
[51] Int. Cl.[7] ................ A61K 31/403; C07D 231/54; C07D 231/56
[52] U.S. Cl. ......................... 514/403; 548/360.1
[58] Field of Search .................. 548/360.1; 514/403

[56] References Cited

U.S. PATENT DOCUMENTS
5,387,602  2/1995  Ferro .
5,783,597  7/1998  Beers et al. .

FOREIGN PATENT DOCUMENTS
26 30 015  7/1976  European Pat. Off. .
WO 98 22442  11/1997  WIPO .
WO98 22442  5/1998  WIPO .

OTHER PUBLICATIONS
J.Med. Chem. 1997 1,2–Diarylpyrroles Aspotent and Selective Inhibitors of Cyclooxygenase–2 Ish K. Khanna et al. pp. 1619 & 1620.

Exp Opin. Invest Drugs (1997) 6(7); pp. 805–809, Nigel d. Staite Future Therapies For Rheumatoid Arthritis.

J.Med. Chem1997, 40, 1347, Thomas D. Penning et al. Synthesis and Biological Evaluation of the 1,5–Diarylpyrazole Class of Cyclooxygenase–2 Inhibitors:Indentification of 4–[5–(4–Methylphenyl)–3–(Trifluoromethyl)–1H– Pyrazol– 1–yl]Benzenesulfonamide(SC–58635,Celecoxib).

J.Med Chem. 1997, 40, 1634–1635, Ish K. Khanna et al., 1,2–Diarylimidazoles as Potent, Cyclooxygenase–2 Selective, and Orally Active Antiinflammatory Agents.

Primary Examiner—Robert W. Ramsuer
Attorney, Agent, or Firm—Kenneth J. Dow

[57] ABSTRACT

This invention is directed to certain 1,3- and 2,3-diarylpyrazole antiinflammatory compounds of the general formulae:

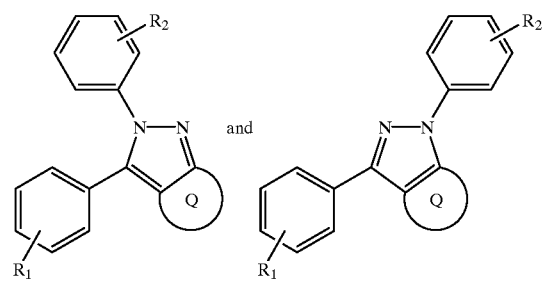

wherein $R_1$ and $R_2$ are independently selected from the group consisting of hydrogen, halogen, $(C_1-C_6)$alkyl, $(C_1-C_6)$alkoxy, nitro, amino, hydroxy, trifluoro, $-S(C_1-C_6)$alkyl, $-SO(C_1-C_6)$alkyl and $-SO_2(C_1-C_6)$alkyl and the fused moiety Q is a group selected from the group consisting of an optionally substituted cyclohexyl and cycloheptyl group as herein described, pharmaceutical compositions containing the compounds, processes for their production and use as COX-2 inhibitor and antiinflammatory agents.

12 Claims, No Drawings

1,3- AND 2,3-DIARYLCYCLOALKANO AND CYCLOALKENO PYRAZOLES AS SELECTIVE INHIBITORS OF CYCLOOXYGENASE-2 AND ANTIINFLAMMATORY AGENTS

This application claims the benefit of U.S. Provisional Application No. 60/106,149, filed Oct. 29, 1998.

FIELD OF THE INVENTION

The present invention is directed to certain new 1,3- and 2,3-diarylpyrazoles fused with cycloalkanes and cycloalkenes, processes for their production and their use as cyclooxygenase-2 (COX-2) inhibitors and antiinflammatory agents.

BACKGROUND OF THE INVENTION

The principal pharmacological effects of nonsteroidal anti-inflammatory drugs (NSAIDs) are due to their ability to inhibit prostaglandin synthesis by blocking cyclooxygenase (COX). Prostaglandins are derived from arachidonic acid and the their biosynthesis occurs in three stages: (1) hydrolysis of arachidonate from phospholipid precursors, most likely catalyzed by phospholipase $A_2$; (2) oxygenation of arachidonate to prostaglandin endoperoxide $H_2$ ($PGH_2$), catalyzed by two closely related isozymes, prostaglandin endoperoxide H synthase-1 and -2 (i.e. cyclooxygenase-1 (COX-1) and COX-2); (3) conversion of $PGH_2$ to a biologically active end-product (e.g. $PGE_2$, $PGF_{2\alpha}$, $PGI_2$) catalyzed by individual enzymes. Compounds which inhibit prostaglandin synthesis are anti-inflammatory, anti-pyretic and analgesic. Common side effects of NSAIDs frequently limit their therapeutic use. Typical side effects associated with NSAID therapy are experienced in the gastrointestinal (GI) tract and in the renal system. These side effects were believed to be inseparable from the pharmacological effects since prostaglandins have cytoprotective effects in the GI tract and also regulate renal blood flow.

The discovery that COX-1 and COX-2 are two isozymes that catalyze the second step in prostaglandin synthesis has provided the possibility to separate the pharmacological effects from the side effects of NSAIDs. Research results suggest that COX-1 and COX-2 belong to separate prostaglandin-forming systems. COX-1 is expressed constitutively in most cells and tissues. The COX-1 dependent pathway can respond instantaneously and produces prostaglandins that regulate acute events such as vascular homeostasis. The synthesis of prostaglandins by COX-1 also helps maintain normal stomach and renal function. COX-2 is only expressed following mitogenic or inflammatory stimuli. Since COX-2 is not expressed in most resting tissues and must be induced, prostaglandins produced by COX-2 are probably involved only secondarily in prolonged physiological reactions. This discovery has now given a reason to believe that the GI and renal side effects of NSAIDs can be avoided.

SUMMARY OF THE INVENTION

The present invention is directed to certain 1,3- and 2,3-diarylpyrazole compounds of the general Formula 1 and Formula 2 as useful anti-inflammatory agents:

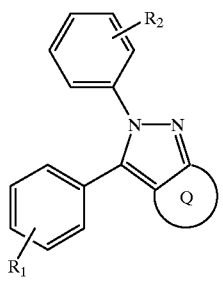

Formula 1

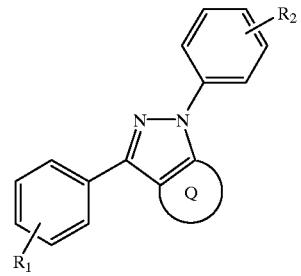

Formula 2 wherein
$R_1$ and $R_2$ are independently selected from the group consisting of hydrogen, halogen, ($C_1$–$C_6$)alkyl, ($C_1$–$C_6$)alkoxy, nitro, amino, hydroxy, trifluoro, —S($C_1$–$C_6$)alkyl, —SO($C_1$–$C_6$)alkyl and —$SO_2$($C_1$–$C_6$)alkyl; and the fused moiety Q is a group selected from the group consisting of an optionally substituted cyclohexyl and cycloheptyl group having the formulae:

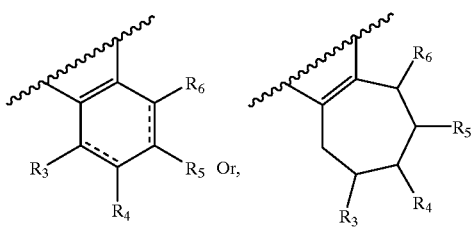

wherein
$R_3$ is selected from the group consisting of hydrogen, halogen, hydroxy and carbonyl;
or $R_3$ and $R_4$ taken together form a moiety selected from the group consisting of —$OCOCH_2$—, —$ONH(CH_3)COCH_2$—, —OCOCH= and —O—;
$R_4$ and $R_5$ are independently selected from the group consisting of hydrogen, halogen, hydroxy, carbonyl, amino, ($C_1$–$C_6$)alkyl, ($C_1$–$C_6$)alkoxy, =NOH, —$NR_7R_8$, —$OCH_3$, —$OCH_2CH_3$, —$OSO_2NHCO_2CH_3$, =$CHCO_2CH_2CH_3$, —$CH_2CO_2H$, —$CH_2CO_2CH_3$, —$CH_2CO_2CH_2CH_3$, —$CH_2CON(CH_3)_2$, —$CH_2CO_2NHCH_3$, —$CHCHCO_2CH_2CH_3$, —$OCON(CH_3)OH$, —$C(COCH_3)_2$, di($C_1$–$C_6$)alkyl and di($C_1$–$C_6$)alkoxy;
$R_6$ is selected from the group consisting of hydrogen, halogen, hydroxy, carbonyl, amino, ($C_1$–$C_6$)alkyl, ($C_1$–$C_6$)alkoxy and optionally substituted carboxyphenyl, wherein substituents on the carboxyphenyl group are selected from the group consisting of halogen, hydroxy, amino, ($C_1$–$C_6$)alkyl and ($C_1$–$C_6$)alkoxy;

or $R_5$ and $R_6$ taken together form a moiety selected from the group consisting of —O— and

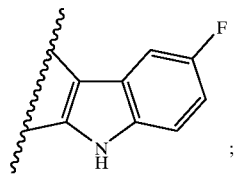

$R_7$ is selected from the group consisting of hydrogen, OH, —OCOCH$_3$, —COCH$_3$ and (C$_1$–C$_6$)alkyl; and $R_8$ is selected from the group consisting of hydrogen, OH, —OCOCH$_3$, —COCH$_3$, (C$_1$–C$_6$)alkyl, —CONH$_2$ and —SO$_2$CH$_3$;

with the proviso that if Q is a cyclohexyl group, then $R_3$ through $R_6$ may not all be hydrogen; and pharmaceutically acceptable salts, esters and pro-drug forms thereof.

The present invention is directed to processes for preparing the instant compounds. The invention is also directed to pharmaceutical compositions containing the compounds. The invention is further directed to a method for alleviating a condition of inflammation in a mammal in need thereof. The invention is still further directed to a method for administering to a mammal an effective amount of a pharmaceutical composition containing a unit dose of the compounds of the present invention in association with a pharmaceutically acceptable carrier.

DETAILED DESCRIPTION OF THE INVENTION

Relative to the above generic description, certain compounds of the general Formula 1 and Formula 2 are preferred wherein $R_1$ and $R_2$ are independently selected from the group consisting of hydrogen, halogen, (C$_1$–C$_6$)alkyl, (C$_1$–C$_6$)alkoxy, trifluoro and —SO$_2$(C$_1$–C$_6$)alkyl; and the fused moiety Q is a group selected from the group consisting of an optionally substituted cyclohexyl and an unsubstituted cycloheptyl group wherein $R_3$ is hydrogen;

$R_4$ and $R_5$ are independently selected from the group consisting of hydrogen, carbonyl, (C$_1$–C$_6$)alkoxy, —OSO$_2$NHCO$_2$CH$_3$, =CHCO$_2$CH$_2$CH$_3$, —CH$_2$CO$_2$H, —CH$_2$CO$_2$CH$_3$, —CH$_2$CO$_2$CH$_2$CH$_3$, —CH$_2$CO$_2$NHCH$_3$ and —CHCHCO$_2$CH$_2$CH$_3$;

$R_6$ is hydrogen;

or $R_5$ and $R_6$ taken together form a moiety selected from the group consisting of —O— and

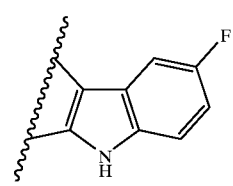

with the proviso that if Q is a cyclohexyl group, then $R_3$ through $R_6$ may not all be hydrogen; and pharmaceutically acceptable salts, esters and pro-drug forms thereof.

Particularly preferred compounds of the general Formula 1 and Formula 2 are shown in Table 1 and Table 2, respectively.

Preferred compounds according to the general Formula 1 are as follows:

TABLE 1

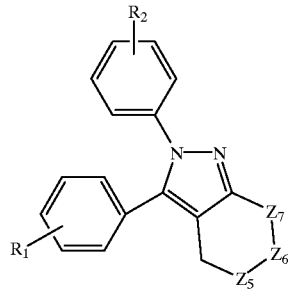

| Ex# | $R_1$ | $R_2$ | $Z_5$ | $Z_6$ | $Z_7$ |
|---|---|---|---|---|---|
| 4b | 4-Cl | 4-SO$_2$Me | CH$_2$ | | HC=CH |
| 5b | 4-F | 4-SO$_2$Me | CH$_2$ | | HC=CH |
| 6-1a | 4-Cl | H | CH$_2$ | CH$_2$ | CH$_2$ |
| 13-1d | 4-Cl | 4-SO$_2$Me | CH$_2$CH$_2$ | CH$_2$ | CH$_2$ |
| 13-1e | 4-Cl | 4-Me | CH$_2$CH$_2$ | CH$_2$ | CH$_2$ |
| 13-1f | 4-Cl | H | CH$_2$CH$_2$ | CH$_2$ | CH$_2$ |
| 13-1g | 4-F | 4-OMe | CH$_2$CH$_2$ | CH$_2$ | CH$_2$ |
| 30d | 4-Cl | 4-SO$_2$Me | CH$_2$ | CH$_2$ | CH$_2$ |
| 32c | 4-CF$_3$ | 4-SO$_2$Me | CH$_2$ | | HC=CH |
| 32d | 4-Cl | 4-SO$_2$Me | CH | | HC=CH |
| 32e | 4-SO$_2$Me | F | CH | | HC=CH |
| 48e | 4-F | 4-SO$_2$Me | CH$_2$ | | Epoxide |
| 52b | 4-Cl | 4-SO$_2$Me | CH$_2$ | C=O | CH$_2$ |

Preferred compounds according to the general Formula 2 are as follows:

TABLE 2

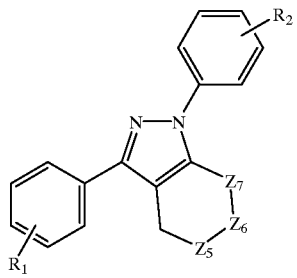

| Ex# | $R_1$ | $R_2$ | $Z_5$ | $Z_6$ | $Z_7$ |
|---|---|---|---|---|---|
| 3-1 | 4-Cl | H | — | CH$_2$ | CH$_2$ |
| 6-1b | 4-Cl | H | CH$_2$ | CH$_2$ | CH$_2$ |
| 8 | 4-Cl | 4-OMe | CH$_2$CH$_2$ | CH$_2$ | CH$_2$ |
| 9 | 4-F | 4-OMe | CH$_2$CH$_2$ | CH$_2$ | CH$_2$ |
| 11 | 4-Cl | 4-Me | CH$_2$CH$_2$ | CH$_2$ | CH$_2$ |
| 12 | 4-Cl | H | CH$_2$CH$_2$ | CH$_2$ | CH$_2$ |
| 13-2b | 4-OMe | H | CH$_2$CH$_2$ | CH$_2$ | CH$_2$ |

TABLE 2-continued

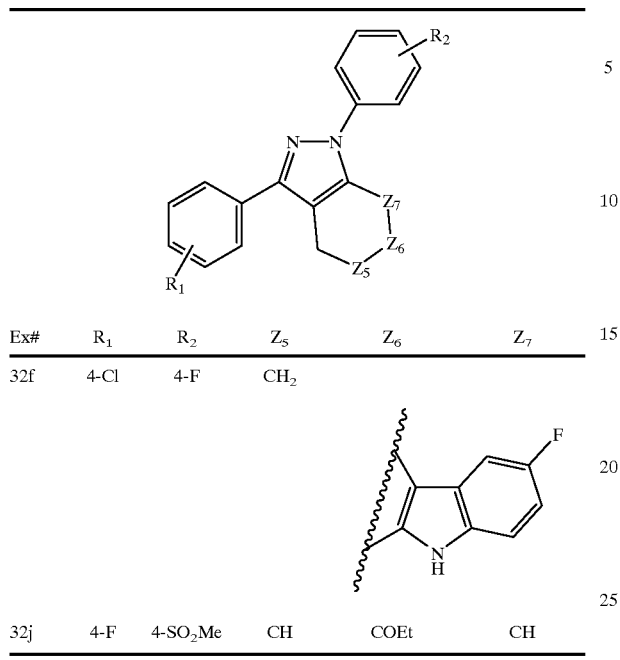

| Ex# | $R_1$ | $R_2$ | $Z_5$ | $Z_6$ | $Z_7$ |
|-----|-------|-------|-------|-------|-------|
| 32f | 4-Cl | 4-F | CH$_2$ | | |
| 32j | 4-F | 4-SO$_2$Me | CH | COEt | CH |

General Synthetic Methods

Representative compounds of the present invention can be synthesized in accordance with the general synthetic methods described and illustrated in the schemes below. Since the schemes are illustrations, the invention should not be construed as being limited by the chemical reactions, conditions and target compounds expressed. Compounds beyond those illustrated may be prepared using these general methods with appropriate reagents and starting materials. The preparation of various starting materials used in the schemes is within the skill of persons versed in the art.

Compounds 1e, 1f, 2c, 2d, 2e, 3d and 3e prepared in accordance with Schemes 1, 2 and 3 may be used as intermediates to prepare compounds having further substitutions in accordance with the general methods set forth in the following Schemes 4 through 10 and by other methods known in the art, all of which are considered to be within the scope of the invention.

Scheme 1

Scheme 1 shows the general synthesis of fused cyclohexyl and cycloheptyl compounds of Formula 2. In accordance with Scheme 1, an appropriately substituted benzoic acid Compound 1a is first treated with oxalyl chloride and then reacted with an appropriately substituted phenyl hydrazine or its acid addition salt from about 0° C. to about RT for about 2 h to about 24 h in a suitable inert solvent, such as ethanol, to give a diphenyl hydrazide Compound 1b. The aldehyde group is then converted to an α-chlorobenzaldehyde phenylhydrazone Compound 1c by treatment with an appropriate reagent such as phosphorus pentachloride or thionyl chloride. Compound 1c is then reacted with an optionally substituted cyclohexyl (wherein n=1), cycloheptyl (wherein n=2) or triethylamine Compound 1d in toluene to obtain Compound 1e. In the present invention, Compound 1d may not be phenyl and includes at least one double bond in the ring and at most two double bonds. Treatment of Compound 1e with chloranil yields a cyclohexylpyrazole or cycloheptylpyrazole Compound 1f of Formula 2.

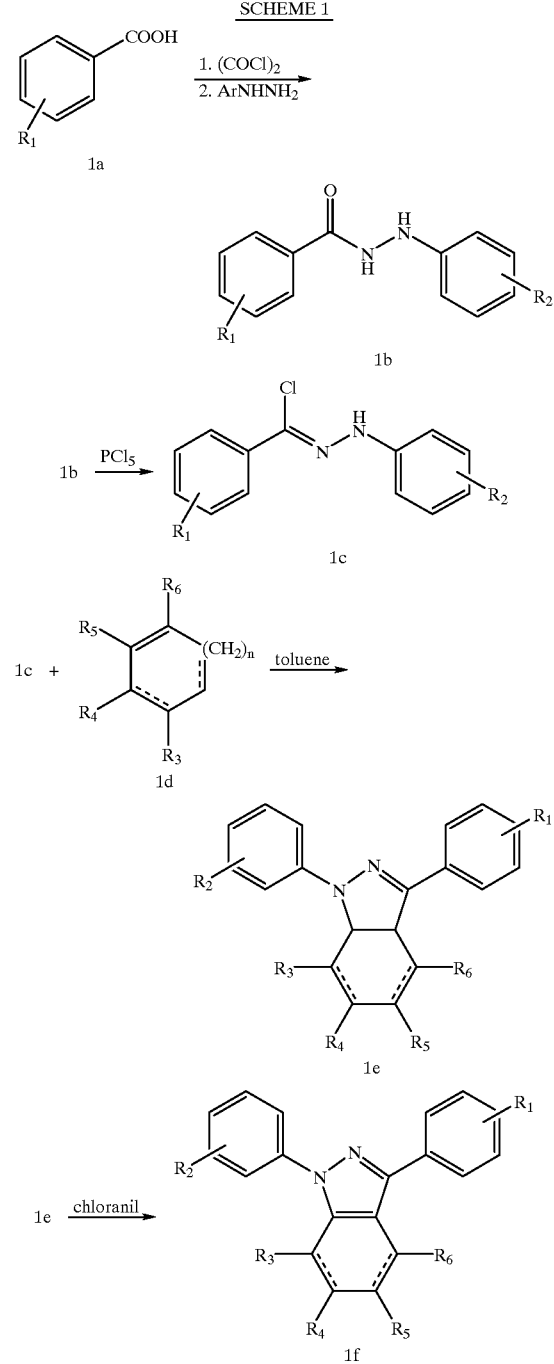

Scheme 2

Alternatively, Scheme 2 can be used to prepare fused cyclohexyl pyrazole compounds of Formulae 1 and 2 by C-acylation of an appropriately substituted cyclohexanone Compound 2a with an appropriately substituted benzoyl chloride Compound 2b to afford a substituted benzoyl cyclohexanone Compound 2c. Lithium bis(trimethylsilyl) amide was used as a base in the acylation reaction. No 0-acylation product was observed. The obtained β-diketone was reacted with phenylhydrazine in refluxing methanol to give a cyclohexylpyrazole Compound 2d and Compound 2e of Formula 1 and Formula 2, respectively.

SCHEME 2

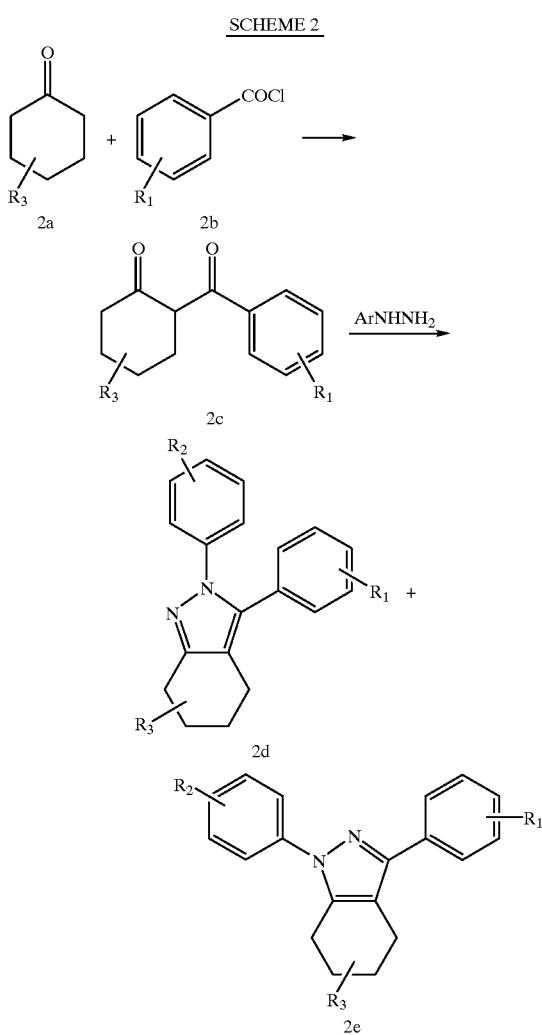

Scheme 3

Scheme 3 illustrates the synthesis of a fused cycloheptyl Compound 3d and Compound 3e of Formula 1 and Formula 2, respectively. C-Acylation of a cycloheptanone Compound 3a with a 4-chlorobenzoyl chloride Compound 3b affords a 2-(4-chlorobenzoyl)-cycloheptanone Compound 3c. Lithium bis(trimethylsilyl)amide was used as a base in the acylation reaction. No O-acylation product was observed. Compound 3c is reacted with phenylhydrazine in refluxing methanol to give a 2,3 pyrazole isomer Compound 3d and a 1,3 pyrazole isomer Compound 3e, wherein Compound 3e was the major product.

SCHEME 3

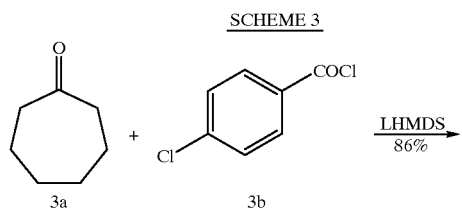

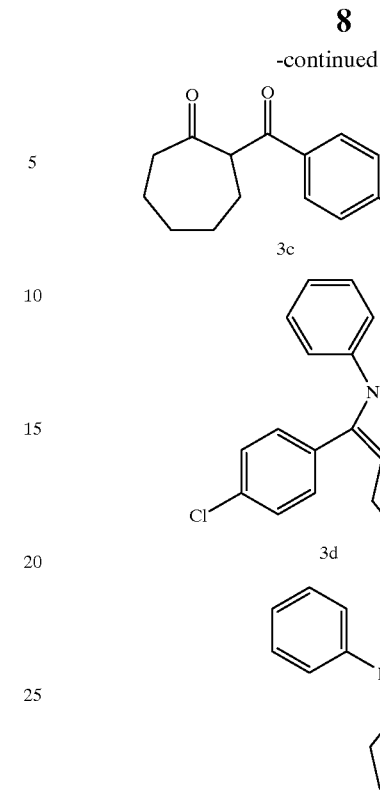

Scheme 4 illustrates reacting an appropriately substituted benzoyl cyclohexanone Compound 2c, prepared in accordance with the method disclosed in Seebach, *Helv. Chimica Acta*, 1981, 64, 3, with an aryl hydrazine compound to obtain a dioxo-ethylene substituted fused cyclohexyl pyrazole Compound 4a and Compound 4b. Compound 4a and Compound 4b can be used as intermediates to make a cyclohexyl or aromatic indazole Compound 4c and Compound 4e, respectively, by reaction with DDQ (2,3-dichloro-5,6-dicyano-1,4-benzoquinone). Furthermore, Compound 4a can be used as an intermediate to prepare a pyrazolo-cyclohexanone Compound 4d by hydrolysis with an acid such as hydrochloric acid.

Alternatively, Scheme 4 illustrates reacting an ethoxy substituted benzoyl cyclohexenone Compound 2c with an aryl hydrazine compound to obtain a pyrazolo-cyclohexene Compound 4f and Compound 4g. Using the procedures described herein, Compound 4f can be used as an intermediate to obtain an aromatic Compound 4h and Compound 4g can be used to obtain an aromatic Compound 4i or the cyclohexanone Compound 4j, as shown in Scheme 4.

SCHEME 4

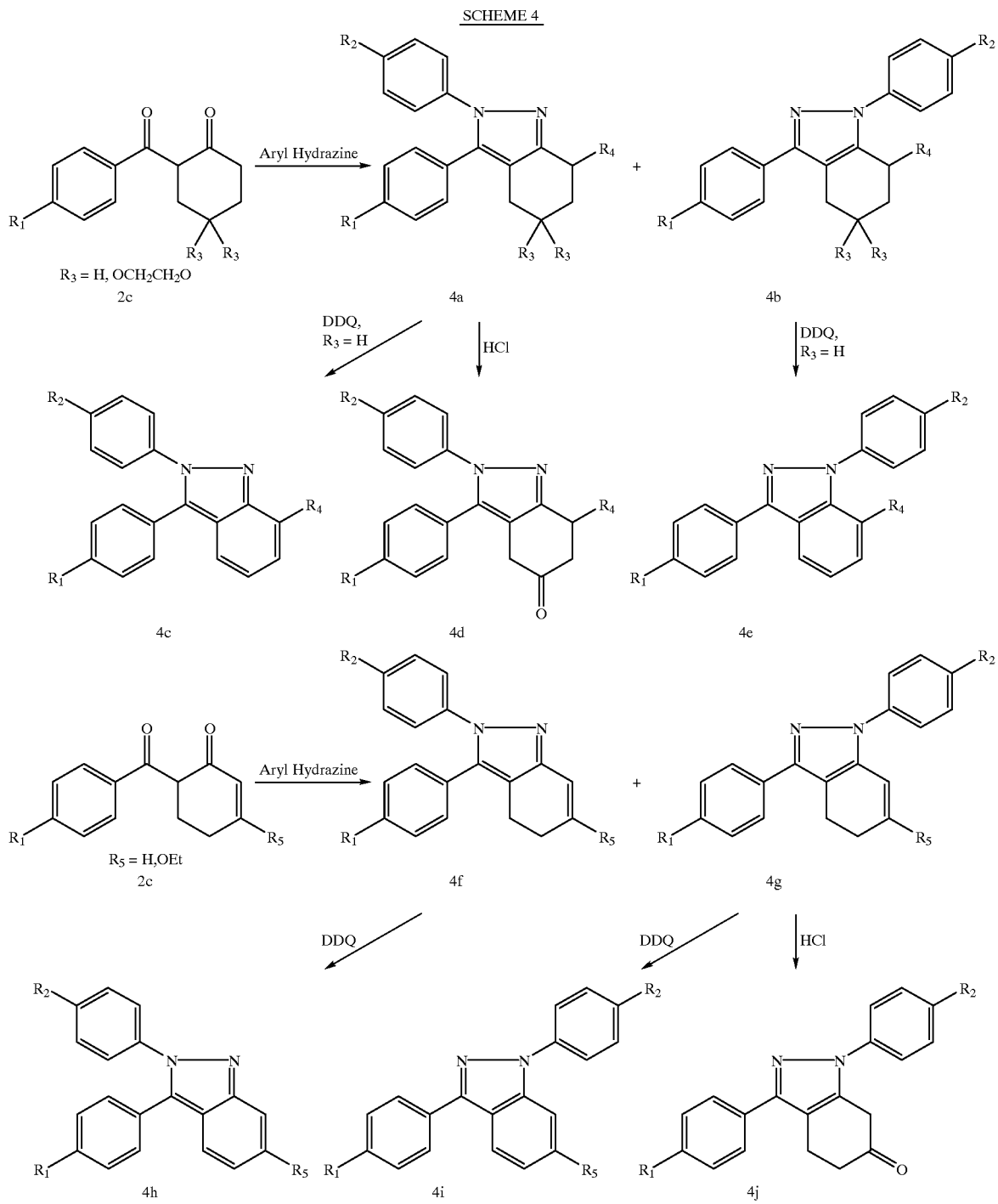

Scheme 5

As shown in Scheme 5, a pyrazolo-cyclohexanone Compound 4d can be used to prepare methylene carboxyl and amide derivatives. Accordingly, Compound 4d is reacted with diethyl phosphonoacetaldehyde diethyl acetal to convert the carbonyl group to an unsaturated α,β aldehyde Compound 5a and Compound 5b in the Wadsworth-Emmons modification of the Wittig reaction. Compound 5a can be converted to a carboxylic acid Compound 5c by direct treatment with a base. Compound 5b can be converted to Compound 5d by hydrogenation. The carboxylic acid Compound 5c can be used as an intermediate to prepare Compound 5f or 5g. Treatment of Compound 5d with a base yields Compound 5e. Compound 5e can be used to obtain Compound 5h and 5i, as further shown in Scheme 5.

SCHEME 5

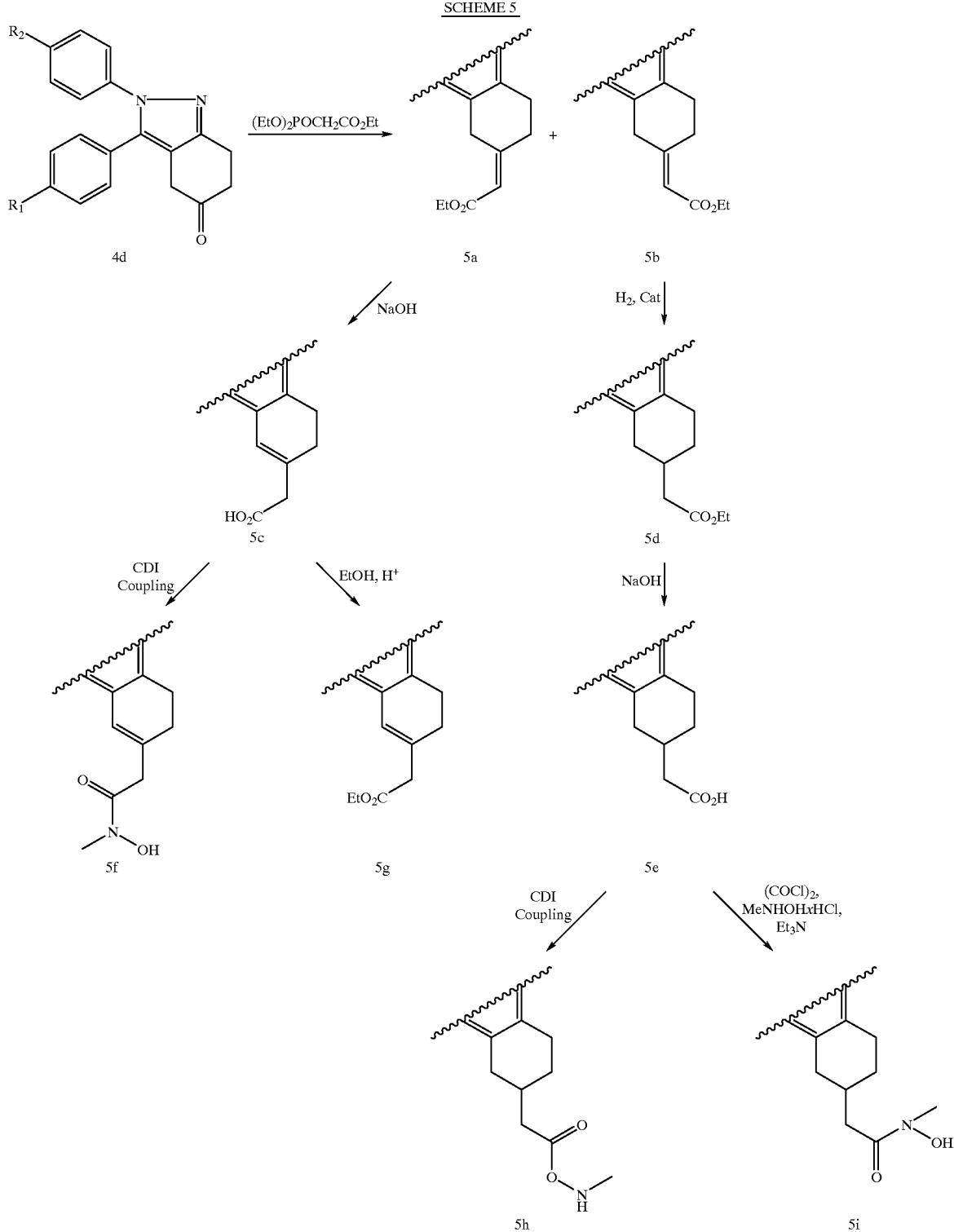

Scheme 6

In accordance with Scheme 6, a pyrazolo-cyclohexanone Compound 4d can be used to prepare amino and hydroxylamino compounds and derivatives thereof. For example, to obtain amino and alkyl-amide compounds as shown in Scheme 6, Compound 4d undergoes reductive amination by ammonolysis or by treatment with an appropriate reagent such as sodium cyanoborohydrate to obtain a cyclohexylamine Compound 6b. Compound 6b can be alkylated to obtain primary or secondary amines or converted to amide or sulfonamide compounds 6h, 6i or 6j by treatment with an acid chloride or sulfonyl chloride, as further shown in Scheme 6.

Alternatively, to obtain hydroxylamino compounds and derivatives thereof, Compound 4d was treated with hydroxylamine hydrochloride and sodium acetate in ethanol to obtain an oxime derivative Compound 6a. Compound 6a can be reduced to obtain a hydroxylamino Compound 6c by treatment with sodium cyanoborohydrate and HCl in methanol. Compound 6c can be used to obtain a variety of derivatives such as the acetyl hydroxylamino compounds 6d and 6e and the hydroxyurea Compound 6f. In addition, Compound 6d can be treated with LiOH to obtain Compound 6g.

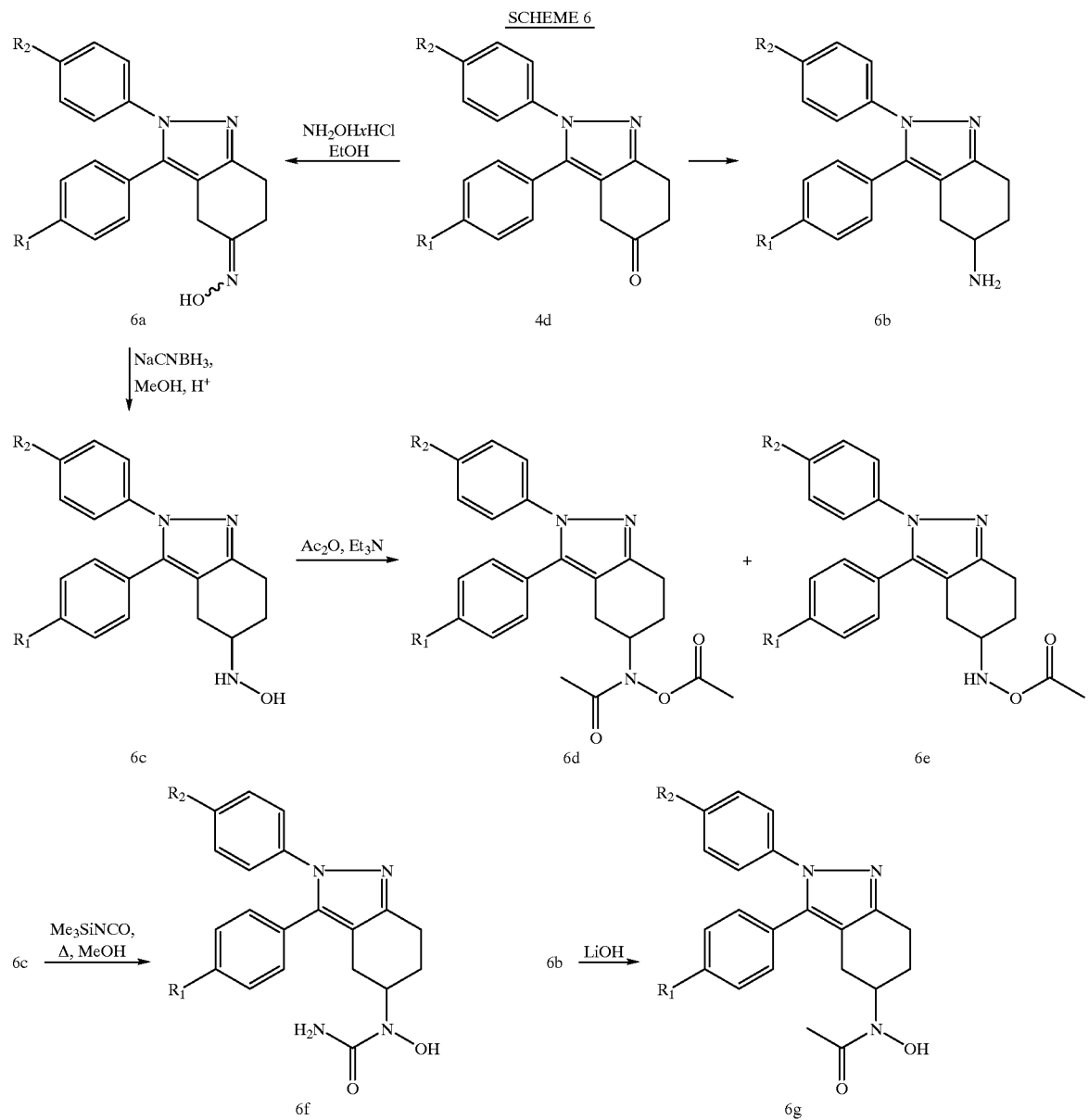

SCHEME 6

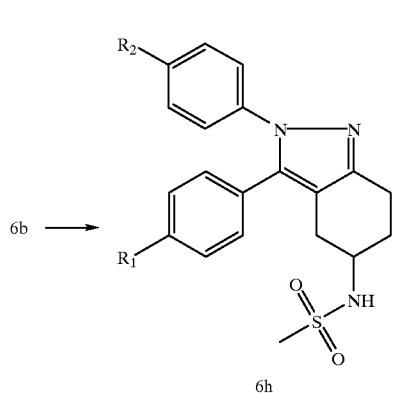

6h

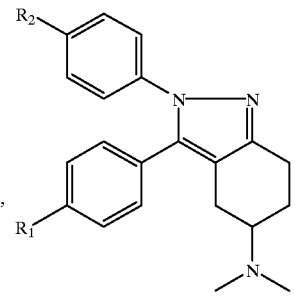

6i

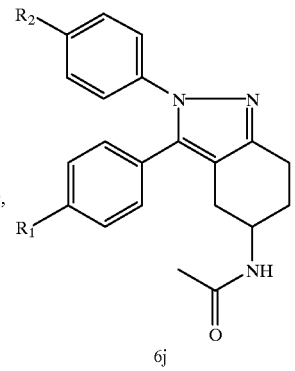

6j

Scheme 7

As shown in Scheme 7, a pyrazolo-cyclohexanone Compound 4d can be used to obtain hydroxyl compounds and derivatives thereof. Accordingly, Compound 4d is treated with diisobutylaluminum hydride in tetrahydrofuran to obtain a hydroxyl derivative Compound 7a. Compound 7a can be used to obtain a methoxycarbonylsulfamoyloxy derivative Compound 7b, a fluoride Compound 7e and a N-hydroxy methylcarbamoyloxy derivative Compound 7f, as shown in Scheme 7. In addition, Compound 7a can be treated with HBr to obtain an alcohol Compound 7c. Compound 7c can be used to further derive an alcohol Compound 7d.

SCHEME 7

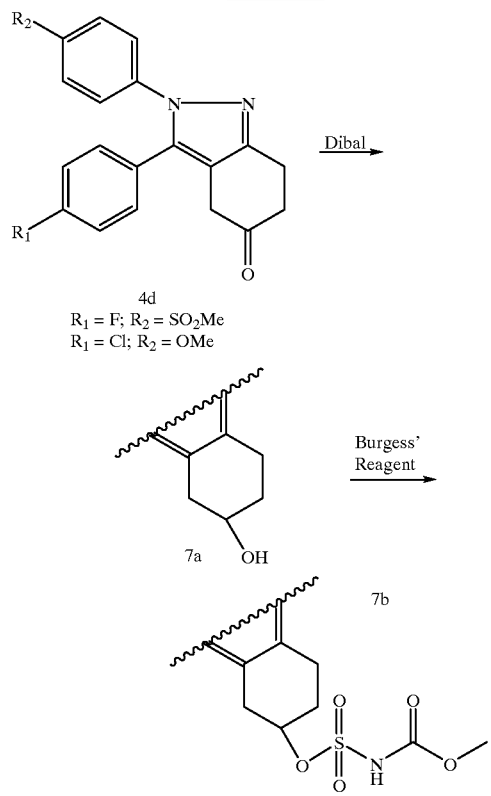

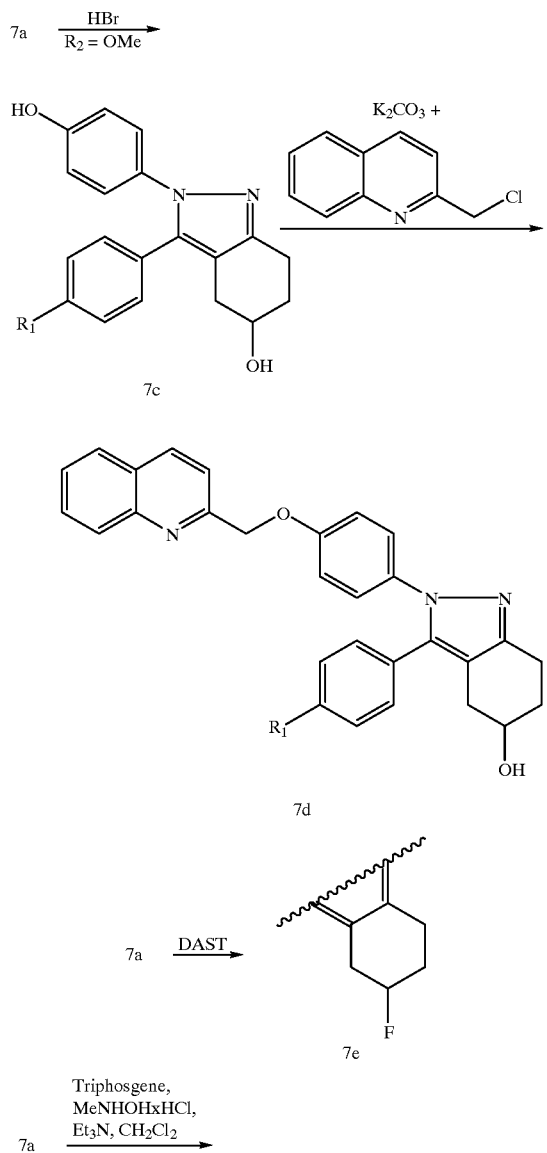

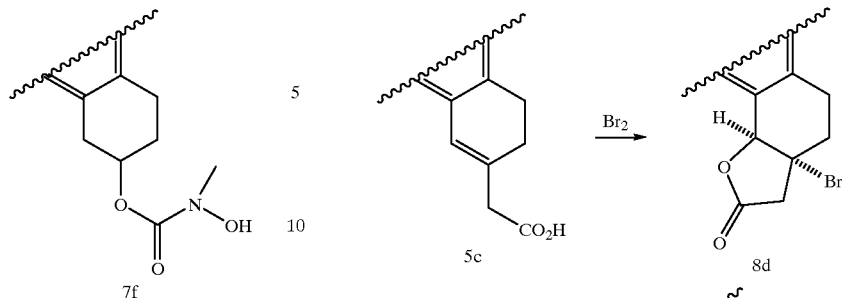

Scheme 8

As shown in Scheme 8, a variety of derivatives can be obtained using Compound 5c or Compound 5g prepared in accordance with Scheme 5.

Treatment of Compound 5g with DDQ (2,3-dichloro-5,6-dicyano-1,4-benzoquinone) yields Compound 8a and Compound 8b. Treatment of Compound 5g with bromine under appropriate conditions yields the bromhydrin Compound 8c. Cyclic compounds such as a furanone Compound 8d, 8e or 8f can be obtained by treatment of Compound 5c with bromine, DDQ or MCPBA, respectively, under appropriate conditions as shown in Scheme 8. As illustrated in Scheme 8, Compound 5c can also be used to derive Compound 8g.

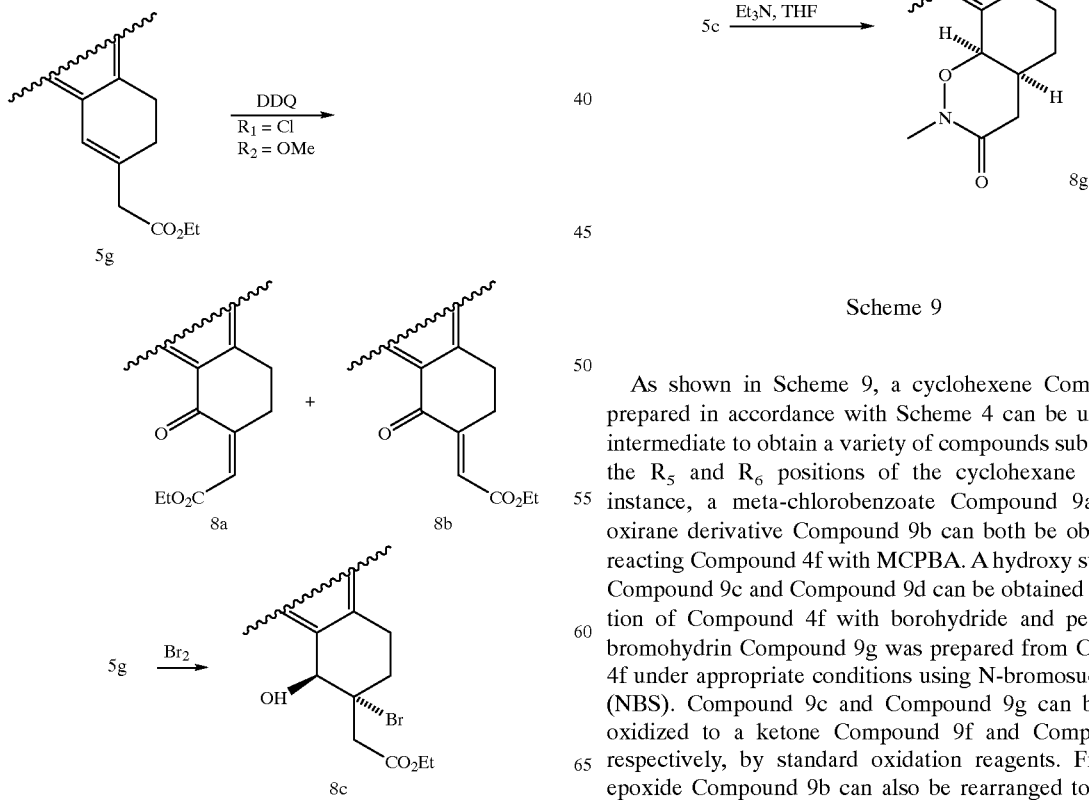

Scheme 9

As shown in Scheme 9, a cyclohexene Compound 4f prepared in accordance with Scheme 4 can be used as an intermediate to obtain a variety of compounds substituted at the $R_5$ and $R_6$ positions of the cyclohexane ring. For instance, a meta-chlorobenzoate Compound 9a and an oxirane derivative Compound 9b can both be obtained by reacting Compound 4f with MCPBA. A hydroxy substituted Compound 9c and Compound 9d can be obtained by reduction of Compound 4f with borohydride and peroxide. A bromohydrin Compound 9g was prepared from Compound 4f under appropriate conditions using N-bromosuccinimide (NBS). Compound 9c and Compound 9g can be further oxidized to a ketone Compound 9f and Compound 9h, respectively, by standard oxidation reagents. Finally, an epoxide Compound 9b can also be rearranged to a ketone Compound 9e.

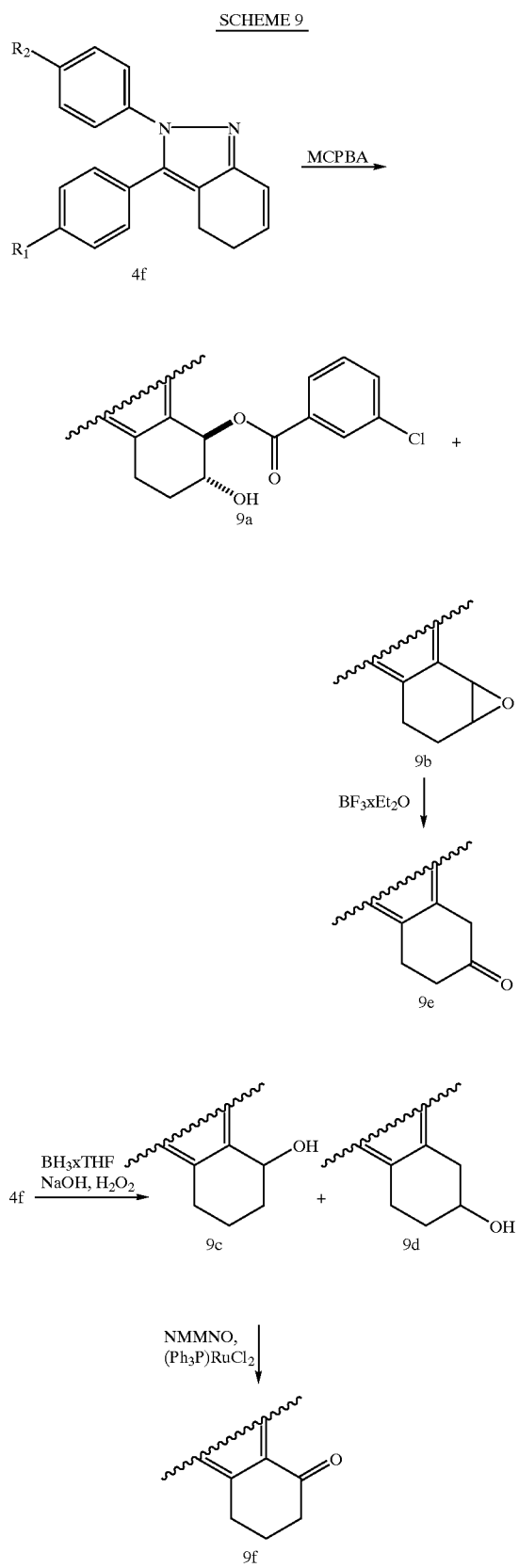
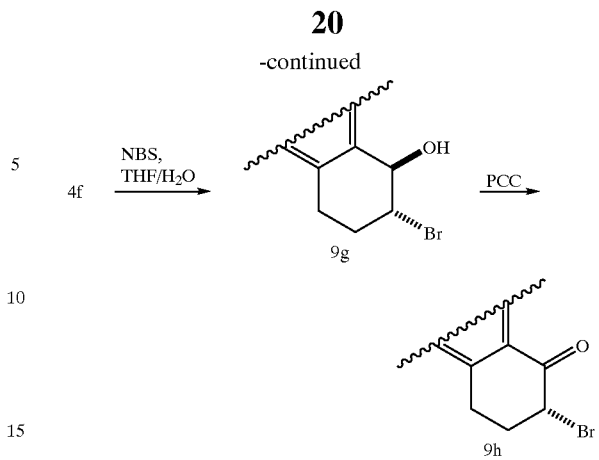

Scheme 10

As shown in Scheme 10, hydroxylamino compounds and derivatives thereof can be obtained by treating Compound 4j with hydroxlyamine hydrochloride and sodium acetate in ethanol to obtain an oxime derivative Compound 10a. Compound 10a can be reduced to obtain the hydroxylamino Compound 10b by treatment with sodium cyanoborohydrate and HCl in methanol. Compound 10b can be used to obtain a variety of derivatives such as Compound 10c, 10e and 10f. Compound 10c can be treated with LiOH to obtain Compound 10d. Compound 10d can be further used to prepare methylene carboxyl and amide derivatives.

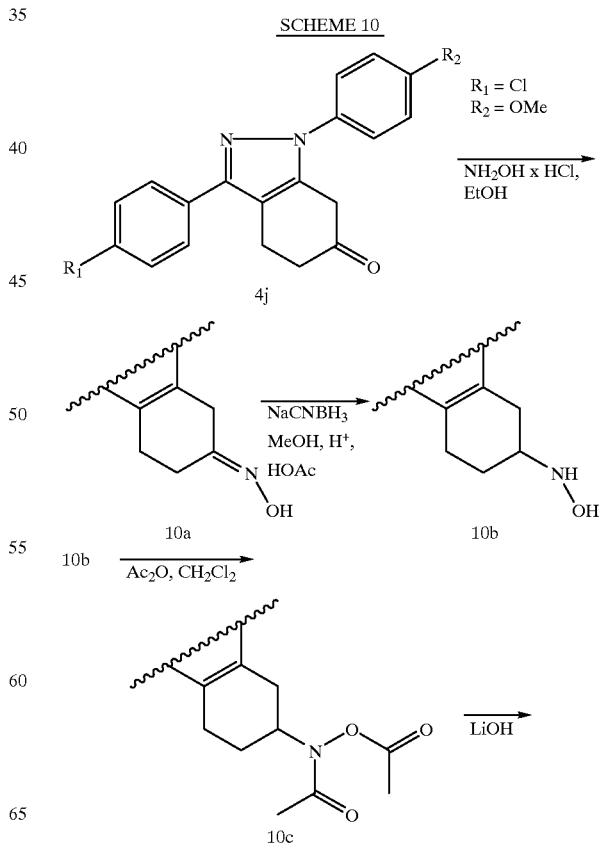

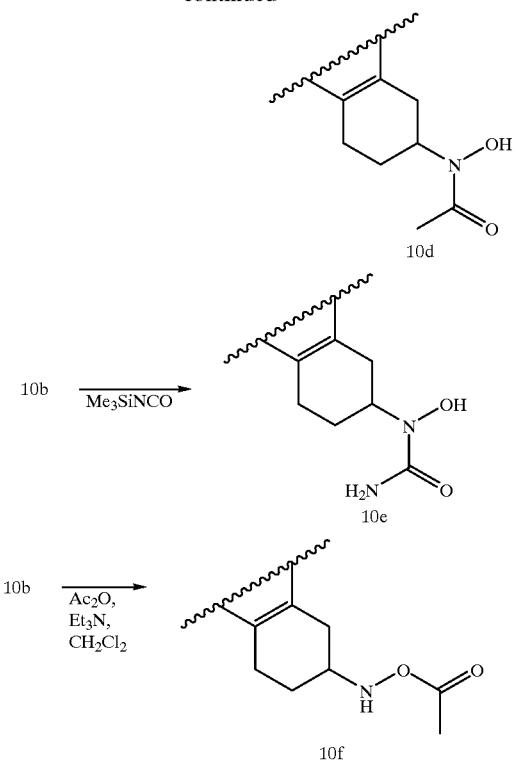

Also provided by the present invention is a method for the preparation of the instant compounds that form by the action of DDQ or an equivalent reagent such as chloranil.

Definitions

The terms used in describing the invention are commonly used and known to those skilled in the art. However, the terms that could have other meanings are herein defined.

"Independently" means that when there are more than one substituent, the substitutents may be different. The term "alkyl" refers to straight, cyclic and branched-chain alkyl groups and "alkoxy" refers to 0-alkyl where alkyl is as defined supra.

In the examples and throughout this application, the following abbreviations have the meanings recited herein:

| | |
|---|---|
| Ac | Acetyl |
| ACN | Acetonitrile |
| Bn | Benzyl |
| Boc | t-Butoxycarbonyl |
| Burgess Reagent | (Carboxysulfamoyl)triethylammonium hydroxide inner salt methyl ester |
| CDI | Carbonyldiimidazole |
| DAST | Diethylaminosulfur trifluoride |
| DDQ | 2,3 Dichloro-5-6-dicyano-1,4-benzoquinone |
| Dibal | Diisobutylaluminum hydride |
| DMF | N,N-dimethylformamide |
| Et | Ethyl |
| Et$_2$O | Diethyl ether |
| EtOAc | Ethyl acetate |
| h | Hour |
| HBSS | Hanks' Balanced Salt Solution |
| HOAc | Acetic acid |
| LAH | Lithium aluminum hydride |
| LDA | Lithium diiopropylamide |
| LHMDS | Lithium hexamethyldisilazide |
| MCPBA | Meta-chloroperoxybenzoic acid |
| MeOH | Methanol |
| Me$_3$SiNCO | Trimethylsilylisocyanate |
| min | Minute |
| MPLC | Medium pressure liquid chromatography |
| NBS | N-Bromo Succinimide |
| NMMNO | 4-Methylmorpholine-N-oxide |
| RT | Room temperature |
| THF | Tetrahydrofuran |

The foregoing reactions are performed in a solvent appropriate to the reagents and materials employed and suitable for the transformation being effected. It is understood by those skilled in the art of organic synthesis that the various substituents present on the molecule must be consistent with the chemical transformations proposed. This will frequently necessitate judgment as to the order of synthetic steps, protection of reactive groups and selection of reaction conditions. Reaction conditions compatible with the substituents employed will be apparent to one skilled in the art, as will be the selection of protecting groups where needed.

From Formula 1 and Formula 2, it is evident that some of the compounds of the invention may have one or more asymmetrical carbon atoms in their structure. It is intended that the present invention includes within its scope the stereochemically pure isomeric forms of the compounds as well as their racemates. Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereospecific reactions.

Suitable pharmaceutical salts are those of inorganic or organic acids, such as hydrochloric acid, hydrobromic acid, hydroiodic acid, sulfuric acid, nitric acid, phosphoric acid, acetic acid, succinic acid, oxalic acid, malic acid and the like.

Suitable salts are also those of inorganic or organic bases, such as KOH, NaOH, Ca(OH)$_2$, Al(OH)$_3$, piperidine, morpholine, ethylamine, triethylamine and the like.

Also included within the scope of the invention are the hydrated forms of the compounds that contain various amounts of water, for instance, the hydrate, hemihydrate and sesquihydrate forms.

The substituted cycloalkano-pyrazole compounds of the invention are capable of inhibiting the COX-2 enzyme pathway to achieve the desired pharmacological result. In preferred practice, the substituted cycloalkano-pyrazole compounds of the pharmaceutical composition are capable of inhibiting both the COX-1 and COX-2 enzyme pathways in the amount in which the compound is present in the composition, when the composition is administered as a unit dose in the appropriate subject in need thereof.

The present invention includes a method for alleviating a condition of inflammation in a subject in need thereof comprising administering to the subject a therapeutically effective amount of the instant compound. In one embodiment of the invention, the condition of inflammation includes, but is not limited to, a condition caused by pain, fever or inflammation. In another embodiment, the condition of inflammation includes, but is not limited to, a condition caused by rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis and osteoarthritis, degenerative joint diseases, gout, ankylosing spondylitis, bursitis, burns or bruising associated with injury and post-surgery. Preferably, the condition of inflammation includes, but is not limited to, rheumatoid arthritis, osteoarthritis or degenerative joint diseases.

When the compounds are employed for the utility herein described, they may be combined with one or more pharmaceutically acceptable carriers, e.g., solvents, diluents, and the like, and may be administered orally in such forms as tablets, capsules, dispersible powders, granules, or suspensions containing for example, from about 0.5% to about 5% of suspending agent, syrups containing, for example, from about 10% to about 50% of sugar, and elixirs containing, for example, from about 20% to about 50% ethanol, and the like, or parenterally in the form of sterile injectable solutions or suspensions containing from about 0.5% to about 5% suspending agent in an isotonic medium. These pharmaceutical preparations may contain, for example, from about 0.5% up to about 90% of the active ingredient in combination with the carrier, more usually between from about 5% to about 60% by weight.

Compositions for topical application may take the form of liquids, creams or gels, containing a therapeutically effective concentration of a compound of the invention admixed with a dermatologically acceptable carrier.

In preparing the compositions in oral dosage form, any of the usual pharmaceutical media may be employed. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacological acceptable salt can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy use in a syringe exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The effective dosage of active ingredient employed may vary depending on the particular compound employed, the mode of administration and the severity of the condition being treated. However, in general, satisfactory results are obtained when the compounds of the invention are administered at a daily dosage from about 0.01 mg/kg to about 500 mg/kg of animal body weight, preferably given in divided doses two to four times a day, or in sustained release form. For most large mammals the total daily dosage is from about 10 mg to about 2000 mg, preferably from about 100 mg to about 1000 mg. Dosage forms suitable for internal use comprise from about 100 mg to about 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. Veterinary dosages correspond to human dosages with the amounts administered being in proportion to the weight of the animal as compared to adult humans.

The production of the above-mentioned pharmaceutical compositions and medicaments is carried out by any method known in the art, for example, by mixing the active ingredients(s) with the diluent(s) to form a pharmaceutical composition (e.g. a granulate) and then forming the composition into the medicament (e.g. tablets).

Typically, the compounds of Formula 1 and Formula 2 are isolated and used as free bases, however the compounds may be isolated and used as their pharmaceutically acceptable salts. Examples of such salts include hydrobromic, hydroiodic, hydrochloric, perchloric, sulfuric, maleic, fumaric, malic, tartaric, citric, benzoic, mandelic, methanesulfonic, hydroethanesulfonic, benzenesulfonic, oxalic, pamoic, 2-naphthalenesulfonic, p-toluenesulfonic, cyclohexanesulfamic and saccharic.

BIOLOGICAL EXAMPLES

The compounds of the invention were evaluated for their ability to inhibit the production of the arachidonic acid by-products in broken and whole cell models.

PROCEDURE 1 AND 2

HUMAN PROSTAGLANDIN $H_2$ SYNTHASE TYPE II (COX-2) WHOLE CELL ASSAY (MULTIPLE CONCENTRATIONS)

Procedures 1 and 2 were used to determine the ability of the compounds to inhibit human prostaglandin $H_2$ synthase type II (COX-2) in a whole cell assay at multiple concentrations as follows:

ECV-304 (human, endothelial, umbilical cord) cells are maintained in culture in a suitable medium, and are trypsinized and plated at a density of 1×106 cells per well of a 96 well plate prior to assay. Approximately 28 h later, 50 μg/ml PMA and 1 mM ionomycin (both final concentrations) are added to each well and incubated for an additional 16 h. Vehicle or test compounds in the amount of 10 mg are incubated with the cells for five minutes prior to initiation of COX-2 enzyme activity by the addition of 30 μM arachidonic acid. Ten minutes later, an aliquot of the supernatant is withdrawn and the amount of $PGE_2$ present quantitated by radioimmunoassay. Activity, reported as percent inhibition of $PGE_2$ produced, is calculated as follows:

$$\% \text{ Inhibition} = \left(1 - \frac{PGE_2 \text{ produced in treated sample}}{PGE_2 \text{ produced in vehicle sample}}\right) \times 100$$

PROCEDURE 3 AND 4

HUMAN PROSTAGLANDIN $H_2$ SYNTHASE TYPE II (hCOX-2) HOMOGENATE ASSAY (SINGLE CONCENTRATION)

Procedures 3 and 4 were used to assess COX-2 activity in a homogenized cell assay as follows:

COS-7 (African Green Monkey Kidney) cells are maintained in a suitable medium, and are trypsinized and plated at a density of 1×10$^6$ cells/well of a 6 well plate prior to assay. Approximately 24 hours later, cells are transiently transfected with a plasmid containing the human COX-2 gene using the lipofectamine method. Two days later, the cell-free homogenate is prepared by subjecting the cells to a polytron followed by centrifugation at 9,000×g. COX activity, initiated by the addition of 30 mM arachidonic acid to the 9,000×g supernatant, is monitored in the presence of vehicle or drug. Product ($PGE_2$) formation is quantitated by radioimmunoassay. Activity, reported as percent inhibition of $PGE_2$ produced, is calculated as follows:

$$\% \text{ Inhibition} = \left(1 - \frac{PGE_2 \text{ produced in treated sample}}{PGE_2 \text{ produced in vehicle sample}}\right) \times 100$$

PROCEDURE 5

HUMAN PLATELET THROMBOXANE $B_2$ PRODUCTION (via COX-1)

Procedure 5 was used to determine thromboxane $B_2$ ($TXB_2$) production (via COX-1) in human platelets as follows:

Draw blood from one volunteer into heparinized tubes then spin at RT for 15 to 20 minutes at 1,000 RPM. Remove the platelet-rich plasma (PRP) and dilute the PRP 1:20 with 0.9% NaCl containing 14.4U heparin/mL. Add 180 μL of the diluted PRP to each well of a 96-well plate and incubate at 37° C. for 5 minutes. Then add 20 μL vehicle (HBSS with 1% DMSO) or drug and incubate for 15 minutes at 37° C. Add 10 μl calcium ionophore and incubate 15 minutes at 37° C. Stop the reaction on slush ice for 5 minutes and assay supernatants immediately for $TXB_2$ production via RIA or EIA.

Prepare all drugs at 10 mM in DMSO by diluting the drug in HBSS at a 1.100 ratio with 1% DMSO to 100 μM. Add 20 μl to PRP (1:10 ratio) to obtain 10 μM final concentration. The calcium ionophore is prepared by using 7 mg/mL free acid calcium ionophore in DMSO, which is warmed until the ionophore goes into solution. Just prior to use, dilute the solution 1:25 with HBSS.

PROCEDURE 6 AND 7

HUMAN PROSTAGLANDIN $H_2$ SYNTHASE— TYPE I (COX-1) HOMOGENATE ASSAY (SINGLE CONCENTRATION)

Procedures 6 and 7 were used to assess COX-1 activity in a homogenized cell assay as follows:

COS-7 (African Green Monkey Kidney) cells are maintained in a suitable medium, and are trypsinized and plated at a density of 1×10$^6$ cells/well of a 6 well plate prior to assay. Approximately 24 hours later, cells are transiently transfected with a plasmid containing the human COX-1 gene using the lipofectamine method. Two days later, the cell-free homogenate is prepared by subjecting the cells to a polytron followed by centrifugation at 9,000×g. COX activity, initiated by the addition of 30 mM arachidonic acid to the 9,000×g supernatant, is monitored in the presence of vehicle or drug. Product ($PGE_2$) formation is quantitated by radioimmunoassay. Activity, reported as percent inhibition of $PGE_2$ produced, is calculated as follows:

$$\% \text{ Inhibition} = \left(1 - \frac{PGE_2 \text{ produced in treated sample}}{PGE_2 \text{ produced in vehicle sample}}\right) \times 100$$

Table 3 and Table 4 each list the experimental results of the foregoing procedures for select compounds of the invention in either $IC_{50}$ (μM) or % inhibition @10 μM. The numbered columns, as shown in each table, reference a specific procedure and indicate the corresponding results as follows:

P1: Procedure 1 COX 2 Whole Cell % Inhibition @10 μM or @3 μM[a]
P2: Procedure 2 COX 2 Whole Cell $IC_{50}$ (μM)
P3: Procedure 4 COX 2 Homogenized Cell % Inhibition @10 μM
P4: Procedure 5 COX 2 Homogenized Cell $IC_{50}$ (μM)
P5: Procedure 3 COX 1 Human Platelet $IC_{50}$ (μM) or % Inhibition @3 μM[b]
P6: Procedure 6 COX 1 Homogenized Cell % Inhibition @10 μM
P7: Procedure 7 COX 1 Homogenized Cell $IC_{50}$ (μM)

TABLE 3

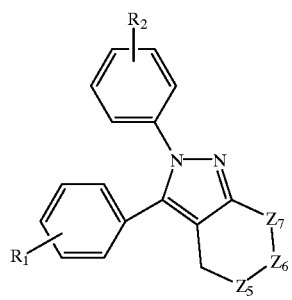

| Ex# | R₁ | R₂ | Z₅ | Z₆ | Z₇ | P1 | P2 | P4 | P5 |
|---|---|---|---|---|---|---|---|---|---|
| 4b | 4-Cl | 4-SO₂Me | CH₂ | HC=CH | — | — | 2.33 | — | >10 |
| 5b | 4-F | 4-SO₂Me | CH₂ | HC=CH | — | — | 4.75 | — | — |
| 6-1a | 4-Cl | H | CH₂ | CH₂ | CH₂ | — | 0.57 | — | >10 |
| 13-1c | 4-Cl | 4-OMe | CH₂CH₂ | CH₂ | CH₂ | — | 19.5 | — | >10 |
| 13-1d | 4-Cl | 4-SO₂Me | CH₂CH₂ | CH₂ | CH₂ | — | 9.41 | 1.5 | >10 |
| 13-1e | 4-Cl | 4-Me | CH₂CH₂ | CH₂ | CH₂ | — | 1.22 | — | 10 |
| 13-1f | 4-Cl | H | CH₂CH₂ | CH₂ | CH₂ | — | 1.38 | — | 5.5 |
| 13-1g | 4-F | 4-OMe | CH₂CH₂ | CH₂ | CH₂ | — | 3.64 | 8.1 | — |
| 13-1h | 4-F | 4-SO₂Me | CH₂CH₂ | CH₂ | CH₂ | — | 10 | — | — |
| 29f[1] | 4-SO₂Me | — | — | — | — | 66[a] | — | — | 6[b] |
| 30b | 4-F | 4-SO₂Me | C(OCH₂)₂ | CH₂ | CH₂ | — | >10 | 21.7 | — |
| 30c | 4-F | 4-OMe | C(OCH₂)₂ | CH₂ | CH₂ | — | >10 | 20.3 | — |
| 30d | 4-Cl | 4-SO₂Me | CH₂ | CH₂ | CH₂ | — | 0.82 | — | >10 |
| 32c | 4-CF₃ | 4-SO₂Me | CH₂ | HC=CH | — | — | 0.61 | — | 24[b] |
| 32d | 4-Cl | 4-SO₂Me | CH | HC=CH | — | — | 0.97 | — | 16 |
| 32e | 4-SO₂Me | F | CH | HC=CH | — | — | 0.32 | — | >10 |
| 48d | 4-Cl | 4-SO₂Me | CH₂ | Epoxide | — | — | 9.58 | — | — |
| 48e | 4-F | 4-SO₂Me | CH₂ | Epoxide | — | — | 6.28 | — | >10 |
| 49d | 4-Cl | 4-SO₂Me | CH₂ | CHOH | CH₂ | — | 10 | — | >10 |
| 52b | 4-Cl | 4-SO₂Me | CH₂ | C=O | CH₂ | — | 1.44 | — | >10 |

[1]Compound 29f was used as a starting material for compounds of Formula 1 and Formula 2, having the structure as shown in Example 29.

[1]Compound 29f was used as a starting material for compounds of Formula 1 and Formula 2, having the structure as shown in Example 29.

TABLE 4

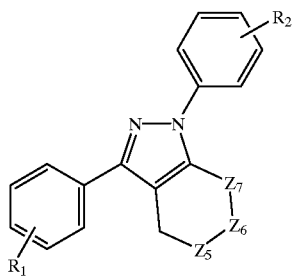

| Ex# | R₁ | R₂ | Z₅ | Z₆ | Z₇ | P1 | P2 | P3 | P4 | P5 | P6 | P7 |
|---|---|---|---|---|---|---|---|---|---|---|---|---|
| 2 | 4-Cl | 4-Cl | — | CH₂ | CH₂ | 0 | >10 | — | — | >10 | — | — |
| 3 | H | H | — | CH₂ | CH₂ | — | 6.2 | — | — | >10 | — | — |
| 3-1 | 4-Cl | H | — | CH₂ | CH₂ | — | 2.59 | — | — | 10 | — | — |
| 4a | 4-Cl | 4-SO₂Me | CH₂ | HC=CH | — | 0 | >10 | — | — | >10 | 32 | — |
| 5a | 4-F | 4-SO₂Me | CH₂ | HC=CH | — | 9 | >10 | 6 | — | >10 | 32 | — |
| 6 | H | H | CH₂ | CH₂ | CH₂ | — | 0.57 | — | — | 0.49 | — | — |
| 6-1b | 4-Cl | H | CH₂ | CH₂ | CH₂ | — | 0.62 | — | — | 10 | — | — |
| 7 | H | H | CH₂CH₂ | CH₂ | CH₂ | — | 0.17 | — | — | 0.12 | — | — |
| 8 | 4-Cl | 4-OMe | CH₂CH₂ | CH₂ | CH₂ | — | 1.56 | 92 | 0.38 | >10 | 25 | 5.3 |
| 9 | 4-F | 4-OMe | CH₂CH₂ | CH₂ | CH₂ | — | 2.51 | — | 2.50 | >10 | 64 | — |
| 10 | 4-Cl | 4-SO₂Me | CH₂CH₂ | CH₂ | CH₂ | 5 | >10 | 26 | — | 10 | 24 | — |
| 11 | 4-Cl | 4-Me | CH₂CH₂ | CH₂ | CH₂ | — | 0.64 | 40 | — | >10 | 74 | — |
| 12 | 4-Cl | H | CH₂CH₂ | CH₂ | CH₂ | — | 0.14 | 74 | — | 1.0 | 93 | — |

TABLE 4-continued

[Structure: 1,3,5-trisubstituted pyrazole with R2-phenyl on N, R1-phenyl at C3, and Z5-CH2-Z6-Z7 ring at C4/C5]

| Ex# | R1 | R2 | Z5 | Z6 | Z7 | P1 | P2 | P3 | P4 | P5 | P6 | P7 |
|---|---|---|---|---|---|---|---|---|---|---|---|---|
| 13 | 4-Cl | 4-Cl | $CH_2CH_2$ | $CH_2$ | $CH_2$ | 3 | 10 | — | — | >10 | — | — |
| 13-1b | 4-Cl | 4-F | $CH_2CH_2$ | $CH_2$ | $CH_2$ | 59 | >10 | — | — | >10 | — | — |
| 13-2b | 4-OMe | H | $CH_2CH_2$ | $CH_2$ | $CH_2$ | — | 1.24 | — | — | 10 | — | — |
| 30e | 4-Cl | 4-$SO_2$Me | $CH_2$ | $CH_2$ | $CH_2$ | 21[a] | — | — | — | — | — | — |
| 32f | 4-Cl | 4-F | $CH_2$ | | | — | 6.2 | — | — | 0.64 | — | — |

[Structure: 5-fluoroindole attachment with wavy bonds at C2 and C3, NH]

| Ex# | R1 | R2 | Z5 | Z6 | Z7 | P1 | P2 | P3 | P4 | P5 | P6 | P7 |
|---|---|---|---|---|---|---|---|---|---|---|---|---|
| 32g | 4-$CF_3$ | 4-$SO_2$Me | $CH_2$ | HC=CH | | — | >10 | — | — | >10 | — | — |
| 32h | 4-F | 4-$SO_2$Me | $CH_2$ | HC=CH | | 13[a] | — | — | — | — | — | — |
| 32i | 4-F | 4-$SO_2$Me | CH | HC=CH | | 12[a] | — | — | — | — | — | — |
| 32j | 4-F | 4-$SO_2$Me | CH | COEt | CH | 87[a] | — | — | — | 35[b] | — | — |
| 32k | 4-Cl | 4-F | CH | | | 29[a] | — | — | — | 22[b] | — | — |

[Structure: 5-fluoroindole attachment with wavy bonds at C2 and C3, NH]

SPECIFIC SYNTHETIC METHODS

In order to more particularly illustrate compounds of the present invention, the following examples are included. The chemical reactions, conditions and target compounds described in these examples are not meant to limit the invention, The examples are meant only to suggest methods of practicing the invention. Those skilled in the art may find other methods of practicing the invention which are obvious to them. Accordingly, compounds beyond those illustrated may be prepared using appropriate reagents, starting materials and methods. Those methods and compounds obtained are also deemed to be within the scope of this invention.

EXAMPLE 1-1

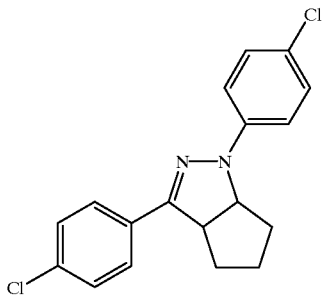

1,3 Di(4-Chlorophenyl)-cis-3a,6a-dihydrocyclopentapyrazole

Compound 1-1

To a solution of α-chloro-4-chlorobenzaldehyde 4-chlorophenylhydrazone (596 mg, 1.99 mMol) and cyclopentene (770 mg, 11.3 mMol) in toluene (5 mL), $Et_3N$ (715 mg, 7.2 mMol) was added. The resulting mixture was refluxed under $N_2$ for about 3 hr and stirred at about RT overnight. The mixture was filtered and then the filtrate was concentrated under reduced pressure to give a crude product that was recrystallized from EtOH to afford Compound 1-1 (543 mg, 82% yield) as a white solid; mp: 192–193° C. $^1$H NMR (300 MHz, $CDCl_3$) δ 1.51 (m, 1H), 1.72 (m, 1H), 1.95 (m, 1H), 1.98 (m, 1H), 2.01 (m, 2H), 4.07 (m, 1H), 4.63 (m, 1H), 7.06 (d, 2H, J=9), 7.22 (d, 2H, J=9), 7.34 (d, 2H, J=9), 7.65 (d, 2H, J=9). IR (KBr) $cm^{-1}$: 2961 (w), 2933 (w), 2864 (w), 1594 (m), 1487 (s). CIMS m/e 331 ($MH^+$). Anal. Cald for $C_{18}H_{16}Cl_2N_2$: C, 65.27; H, 4.87; N, 8.46. Found: C, 65.13; H, 4.85; N, 8.34.

Following the general procedure of Example 1-1, compounds of the present invention such as those set forth in Examples 1-2 to 1-10 were also prepared using appropriate reagents and starting materials.

EXAMPLE 1-2

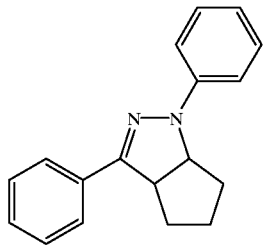

1,3-Diphenyl-cis-3a,6a-dihydrocyclopentapyrazole

Compound 1-2

From α-chlorobenzaldehyde phenylhydrazone (300 mg, 1.3 mMol), cyclopentene (531 mg, 7.8 mMol) in toluene (30 mL) and $Et_3N$ (1 mL), Compound 1-2 (220 mg, 65% yield) was obtained as a white solid after column chromatography (9:1 hexane:dichloromethane); mp: 138–139° C. $^1$H NMR (300 MHz, $CDCl_3$) δ 1.52 (m, 1H), 1.72 (m, 1H), 1.95 (m, 3H), 2.16 (m, 1H), 4.12 (m, 1H), 4.63 (m, 1H), 6.81 (t, 1H, J=9), 7.22 (d, 2H, J=9), 7.35 (m, 3H), 7.40 (m, 2H), 7.78 (d, 2H, J=9). IR (KBr) $cm^{-1}$: 2961 (w), 2933 (w), 2864 (w), 1594 (m), 1487 (s). CIMS m/e 263 ($MH^+$).

EXAMPLE 1-3

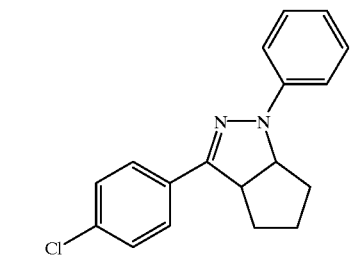

3-(4-Chlorophenyl)-1-phenyl-cis-3a,7a-dihydrocyclopentapyrazole

Compound 1-3

From α-chloro-4-chlorobenzaldehyde phenylhydrazone (528 mg, 1.99 mMol), cyclopentene (770 mg, 11.3 mMol) and $Et_3N$ (715 mg, 7.2 mMol) in toluene (5 mL), Compound 1-3 (283 mg, 48% yield) was obtained as a white solid; mp: 142–144° C. $^1$H NMR (300 MHz, $CDCl_3$) δ 1.52 (m, 2H), 1.73 (m, 1H), 1.97 (m, 2H), 2.12 (m, 1H), 4.06 (m, 1H), 4.70 (m, 1H), 6.83 (t, 1H, J=7), 7.15 (d, 2H, J=9), 7.28 (t, 2H, J=7), 7.34 (d, 2H, J=9), 7.68 (d, 2H, J=9). IR (KBr) $cm^{-1}$: 2932 (w), 1593 (s), 1501 (s), 1489 (s). CIMS m/e 297 ($MH^+$). Anal. Cald for $C_{18}H_{17}ClN_2$: C, 72.84; H, 5.77; N, 9.44. Found: C, 72.73; H, 5.92; N. 9.34.

EXAMPLE 1-4

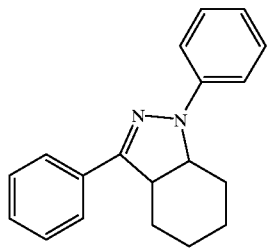

1,3-Diphenyl-cis-3a,7a-dihydrocyclohexapyrazole

Compound 1-4

From α-chlorobenzaldehyde phenylhydrazone (1 g, 4.33 mMol), cyclohexene (2.13 g, 26 mMol) in toluene (30 mL) and $Et_3N$ (1 mL), Compound 1-4 (745 mg, 62% yield) was obtained as a white solid after column chromatography (9:1 hexane:dichloromethane); mp: 73–74° C. $^1$H NMR (300 MHz, $CDC_3$) δ 1.30–1.70 (m, 5H), 1.80–2.05 (m, 3H), 3.51 (m, 1H), 4.05 (m, 1H), 6.98 (t, 1H, J=9), 7.22 (d, 2H, J=9), 7.28–7.42 (m, 5H), 7.76 (d, 2H, J=9). IR (KBr) $cm^{-1}$: 2933 (w), 2864 (w), 1597 (m), 1557 (s). CIMS m/e 277 ($MH^+$). Anal. Cald for $C_{19}H_{20}N_2$: C, 82.57; H, 7.29; N, 10.14. Found: C, 82.63; H, 7.31; N, 10.23.

EXAMPLE 1-5

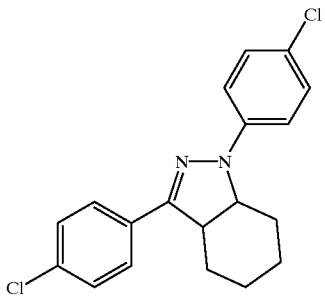

1,3-Di-(4-Chlorophenyl)-cis-3a,7a-dihydrocyclohexapyrazole

Compound 1-5

From α-chloro-4-chlorobenzaldehyde 4-chlorophenylhydrazone (596 mg, 1.99 mMol), cyclohexene (928 mg, 11.3 mMol) and $Et_3N$ (715 mg, 7.2 mMol) in toluene (5 mL), Compound 1-5 (17.4 mg, 2.5% yield) was obtained as a white solid; mp: 146–147° C. $^1$H NMR (300 MHz, $CDCl_3$) δ 1.25 (m, 1H), 1.53 (m, 4H), 1.86 (m, 3H), 3.50 (m, 1H), 4.05 (m, 1H), 7.14 (d, 2H, J=9), 7.26 (d, 2H, J=9), 7.35 (d, 2H, J=9), 7.63 (d, 2H, J=9). IR (KBr) $cm^{-1}$: 2945 (m), 1594 (s), 1489 (s). CIMS m/e 345 ($MH^+$). Anal. Cald for $C_{19}H_{18}Cl_2N_2$: C, 66.09; H, 5.26; N, 8.11. Found: C, 66.34; H, 5.27; N, 8.05.

EXAMPLE 1-6

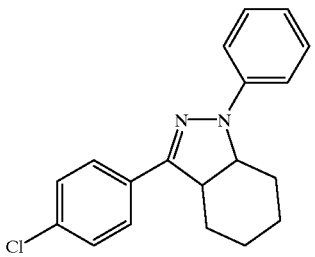

3-(4-Chlorophenyl)-1-phenyl-cis-3a,7a-dihydrocyclohexapyrazole

Compound 1-6

From α-chloro-4-chlorobenzaldehyde phenylhydrazone (528 mg, 1.99 mMol), cyclohexene (928 mg, 11.3 mMol) and $Et_3N$ (715 mg, 7.2 mMol) in toluene (5 mL), Compound 1-6 (110 mg, 17.8% yield) was obtained as a foam. $^1$H NMR (300 MHz, $CDCl_3$) δ 1.42 (m, 1H), 1.54 (m, 4H), 1.86 (m, 2H), 1.94 (m, 1H) 3.47 (m, 1H), 4.06 (m, 1H), 6.97 (t, 1H, J=7), 7.24 (t, 2H, J=7), 7.29 (d, 2H, J=9), 7.45 (d, 2H, J=9), 7.65 (d, 2H, J=9). IR (KBr) $cm^{-1}$: 2936 (m), 1598 (s), 1491 (s). CIMS m/e 311 ($MH^+$). Anal. Cald for $C_{19}H_{19}ClN_2$: C, 73.00; H, 6.19; N, 8.96. Found: C, 72.92; H, 6.05; N, 8.94.

EXAMPLE 1-7

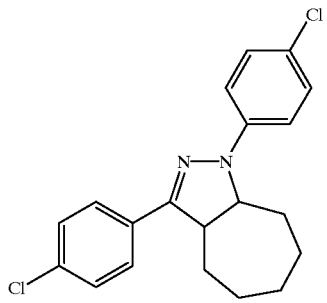

1,3-Di-(4-Chlorophenyl)-cis-3a,8a-dihydrocycloheptapyrazole

Compound 1-7

From μ-chloro-4-chlorobenzaldehyde 4-chlorophenylhydrazone (596 mg, 1.99 mMol), cycloheptene (1.086 g, 11.3 mMol) and $Et_3N$ (715 mg, 7.2 mMol) in toluene (5 mL), Compound 1-7 (516 mg, 72% yield) was obtained as a white solid; mp: 205–206° C. $^1$H NMR (300 MHz, $CDCl_3$) δ 1.49 (m, 6H), 1.89 (m, 2H), 2.15 (m, 2H), 3.88 (m, 1H), 4.42 (m, 1H), 7.08 (d, 2H, J=9), 7.22 (d, 2H, J=9), 7.34 (d, 2H, J=9), 7.59 (d, 2H, J=9). IR (KBr) $cm^{-1}$: 2921 (m), 1593 (s), 1485 (s). CIMS m/e 359 ($MH^+$). Anal. Cald for $C_{20}H_{20}Cl_2N_2$: C, 66.86; H, 5.61; N, 7.80. Found: C, 66.63; H, 5.59; N, 7.70.

EXAMPLE 1-8

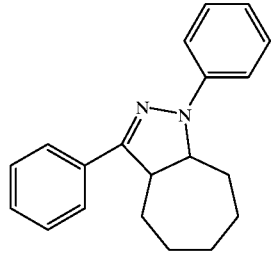

1,3-Diphenyl-cis-3a,8a-dihydrocycloheptapyrazole

Compound 1-8

From α-chlorobenzaldehyde phenylhydrazone (300 mg, 1.3 mMol), cycloheptene (750 mg, 7.8 mMol) in toluene (30 mL) and $Et_3N$ (1 mL), Compound 1-8 (246 mg, 65% yield) was obtained as a white solid after column chromatography (9:1 hexane:dichloromethane); mp: 174–176° C. $^1$H NMR (300 MHz, $CDCl_3$) δ 1.40–1.80 (m, 6H), 1.90 (m, 2H), 2.05 (m, 2H), 3.96 (m, 1H), 4.45 (m, 1H), 6.85 (t, 1H, J=8), 7.18 (d, 2H, J=9), 7.20–7.40 (m, 5H), 7.67 (d, 2H, J=9). IR (KBr) $cm^{-1}$: 2924 (w), 2847 (w), 1596 (m), 1557 (s). CIMS m/e 291 ($MH^+$). Anal. Cald for $C_{20}H_{22}N_2 \cdot 0.1H_2O$: C 82.21; H 7.66; N 9.59. Found: C 82.25; H 7.46; N 9.62.

EXAMPLE 1-9

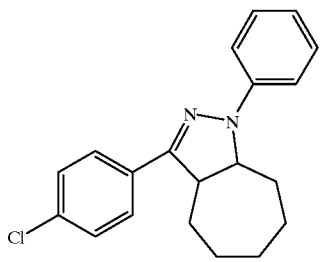

3-(4-Chlorophenyl)-1-phenyl-cis-3a,8a-dihydrocycloheptapyrazole

Compound 1-9

From β-chloro-4-chlorobenzaldehyde phenylhydrazone (365 mg, 1.38 mMol), cycloheptene (740 mg, 7.7 mMol) and Et$_3$N (508 mg, 5 mMol) in toluene (5 mL), Compound 1-9 (214 mg, 48% yield) was obtained as a white solid; mp: 160–161° C. $^1$H NMR (300 MHz, CDCl$_3$) δ 1.47 (m, 6H), 1.88 (m, 2H), 2.04 (m, 2H), 3.91 (m, 1H), 4.44 (m, 1H), 6.86 (t, 1H, J=7), 7.19 (t, 2H, J=7), 7.28 (d, 2H, J=9), 7.33 (d, 2H, J=9), 7.61 (d, 2H, J=9). IR (KBr) cm$^{-1}$: 3427 (w), 2927 (m), 1598 (s), 1498 (s). CIMS m/e 325 (MH$^+$). Anal. Cald for C$_{20}$H$_{21}$ClN$_2$•0.3EtOAc: C, 72.49; H, 6.71; N, 7.97. Found: C, 72.44; H, 6.39; N, 8.36.

EXAMPLE 1-10

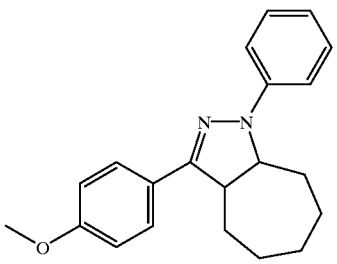

3-(4-Methoxyphenyl)-1-phenyl-cis-3a,8a-dihydrocycloheptapyrazole

Compound 1-10

From α-chloro-4-methoxybenzaldehyde phenylhydrazone (365 mg, 1.38 mMol), cycloheptene (740 mg, 7.7 mMol) and Et$_3$N (508 mg, 5 mMol) in toluene (5 mL), Compound 1-10 (214 mg, 48% yield) was obtained as a white solid; mp: 160–161° C. $^1$H NMR (300 MHz, CDCl$_3$) δ 1.47 (m, 6H), 1.88 (m, 2H), 2.04 (m, 2H), 3.91 (m, 1H), 4.44 (m, 1H), 6.86 (t, 1H, J=7), 7.19 (t, 2H, J=7), 7.28 (d, 2H, J=9), 7.33 (d, 2H, J=9), 7.61 (d, 2H, J=9). IR (KBr) cm$^{-1}$: 3427 (w), 2927 (m), 1598 (s), 1498 (s). CIMS m/e 325 (MH$^+$). Anal. Cald for C$_{20}$H$_{21}$ClN$_2$•0.3EtOAc: C, 72.49; H, 6.71; N, 7.97. Found: C, 72.44; H, 6.39; N, 8.36.

EXAMPLE 2

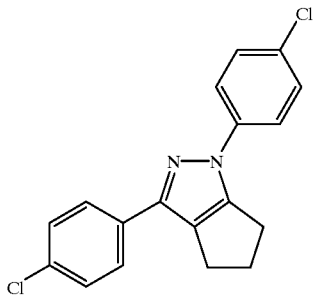

1,3-Di-(4-Chlorophenyl)-cyclopenta-[1,2-d]-pyrazole

Compound 2

To a solution of Compound 1-1 (212 mg, 0.64 mMol) in xylene (25 mL), tetrachloro-1,4-benzoquinone (315 mg, 1.28 mMol) was added. The resulting mixture was heated to reflux under N$_2$ for about 72 h. The mixture was diluted with hexane (25 mL) and chromatographed (EtOAc-hexane) to afford Compound 2 (34 mg, 16% yield) as a white solid; mp: 171–173° C. $^1$H NMR (300 MHz, CDCl$_3$) δ 2.71 (m, 2H), 2.90 (m, 2H), 3.03 (m, 2H), 7.36(d, 2H, J=9), 7.41 (d, 2H, J=9), 7.65 (d, 2H, J=9), 7.78 (d, 2H, J=9). IR (KBr) cm$^{-1}$: 3426 (w), 2971 (w), 1595 (m), 1501 (s). CIMS m/e 329 (MH$^+$). Anal. Cald for C$_{18}$H$_{14}$Cl$_2$N$_2$: C, 65.67; H, 4.29; N, 8.51. Found: C, 65.34; H, 4.32; N, 8.46.

EXAMPLE 3

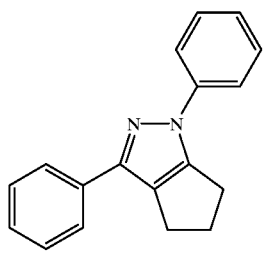

1,3-Diphenyl-cyclopenta-[1,2-d]-pyrazole

Compound 3

Compound 1-1 (80 mg, 0.305 mMol) was mixed with tetrachloro-1,4-benzoquinone (150 mg, 0.61 mMol) in xylene (15 mL) using the procedure of Example 2. Compound 3 (25 mg, 32% yield) was obtained as a white solid; mp: 158–159° C. $^1$H NMR (300 MHz, CDCl$_3$) δ 2.67 (quint, 2H, J=7), 2.91 (t, 2H, J=7), 3.02 (t, 2H, J=7), 7.20–7.32 (m, 2H), 7.41 (m, 4H), 7.71 (dd, 2H, J=9, 1), 7.87 (dd, 2H, J=9, 1). IR (KBr) cm$^{-1}$: 2971 (w), 1598 (m), 1505 (s). CIMS m/e 261 (MH$^+$). Anal. Cald for C$_{18}$H$_{16}$N$_2$•0.4EtOAc: C, 79.64; H, 6.55; N, 9.48. Found: C, 79.81; H, 6.23; N, 9.78.

EXAMPLE 3-1

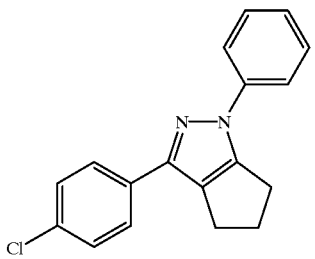

3-(4-Chlorophenyl)-1-phenyl-cyclopenta-[1,2-d]-pyrazole

Compound 3-1

Compound 1-3 (593.6 mg, 2.0 mMol), tetrachloro-1,4-benzoquinone (492 mg, 4.0 mMol) and toluene (25 mL) were combined and refluxed for about 27 h. The resulting mixture was purified by chromatography (silica gel, 1:1 toluene:hexane) to afford Compound 3-1 (587.3 mg, 99.6% yield); mp: 126–127° C. Anal. Cald for $C_{18}H_{15}N_2$: C, 73.34; H, 5.13; N, 9.50. Found: C, 73.09; H, 5.24; N, 9.43.

EXAMPLE 4

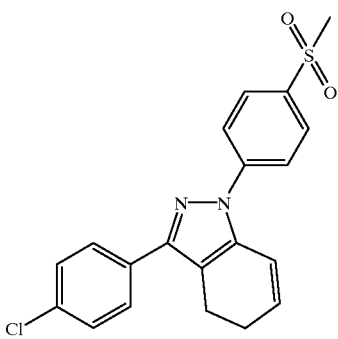

3-(4-Chlorophenyl)-4,5-dihydro-1-(4-methylsulfonylphenyl)-1H-indazole

Compound 4a

A solution of 6-(4-chlorobenzoyl)-cyclohex-2-en-1-one (501 mg, 2 mMol), 4-methylsulfonylphenylhydrazine (372.5 mg, 2 mMol) in toluene (50 mL) and glacial HOAc (2 mL) was refluxed for about 1 h and stirred at about RT overnight. The resulting mixture was poured into water and extracted with EtOAc. The organic layer was washed with water and then dried over $MgSO_4$. The resulting mixture was concentrated under reduced pressure to give a solid. The crude product was purified by column chromatography (silica gel, EtOAc:hexane) to afford Compound 4a (22.5 mg, 2.9% yield) as a white solid; mp: 164–165° C. $^1$H NMR (300 MHz, $CDCl_3$) δ 2.52 (m, 2H), 2.94 (m, 2H), 3.10 (s, 3H), 6.18 (m, 1H), 6.60 (d, 1H, J=9), 7.42 (d, 2H, J=9), 7.71 (d, 2H, J=9), 7.99 (d, 2H, J=9), 8.07 (d, 2H, J=9). IR (KBr) $cm^{-1}$: 2939 (w), 1594 (s), 1501 (m). CIMS m/e 385 (MH$^+$). Anal. Cald for $C_{20}H_{17}ClN_2O_2S$•0.2$H_2O$: C, 61.83; H, 4.51; N, 7.21. Found: C, 61.75; H, 4.39; N, 7.06.

Following the general procedure of Example 4, Compound 4b having the structure of Formula 1 was prepared using appropriate reagents and starting materials.

EXAMPLE 5

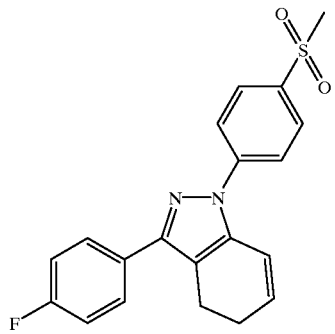

3-(4-Fluorophenyl)-4,5-dihydro-1-(4-methylsulfonylphenyl)-1H-indazole

Compound 5a

From a mixture of 6-(4-fluorobenzoyl)-cyclohex-2-en-1-one (468.5 mg, 2 mMol), 4-methylsulfonylphenylhydrazine (372.5 mg, 2 mMol) in toluene (50 mL) and glac. HOAc (2 mL), Compound 5b (20 mg, 2.7% yield) was obtained as a white solid mp: 175–177° C. $^1$H NMR (300 MHz, $CDCl_3$) δ 2.49 (m, 2H), 2.94 (t, 2H, J=9), 3.10 (s, 3H), 6.17 (m, 1H), 6.60 (d, 1H, J=9), 7.15 (t, 2H, J=9), 7.75 (t, 2H, J=9), 7.79 (d, 2H, J=9), 8.07 (d, 2H, J=9). IR (KBr) $cm^{-1}$: 2996 (w), 1592 (s), 1511 (m). CIMS m/e 369 (MH$^+$). Anal. Cald for $C_{20}H_{17}FN_2O_2S$•0.55$H_2O$: C, 65.20; H, 4.65; N, 7.60. Found: C, 64.86; H, 4.66; N, 7.23.

Following the general procedure of Example 5, Compound 5b having the structure of Formula 1 was prepared using appropriate reagents and starting materials.

EXAMPLE 6

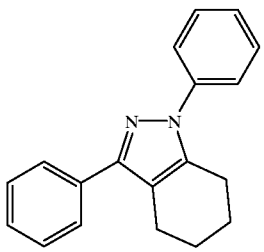

1,3-Diphenyl-cyclohexa-[1,2-d]-pyrazole

Compound 6

To Compound 1-4 (334 mg, 1.21 mMol), tetrachloro-1,4-benzoquinone (595 mg, 2.42 mMol) in xylene (30 mL) was added using the procedure of Example 2. Compound 6 (250 mg, 75% yield) was obtained as a white solid; mp: 127–129° C. $^1$H NMR (300 MHz, $CDCl_3$) δ 1.85 (m, 4H), 2.82 (m, 2H), 7.33 (m, 2H), 7.41 (m, 4H), 7.57 (d, 2H, J=9), 7.82 (d, 2H, J=9). CIMS m/e 275 (MH$^+$). Anal. Cald for $C_{18}H_{16}N_2$•0.1$H_2O$: C, 82.63; H, 6.64; N, 10.14. Found: C, 82.37; H, 6.62; N, 10.04.

EXAMPLE 6-1

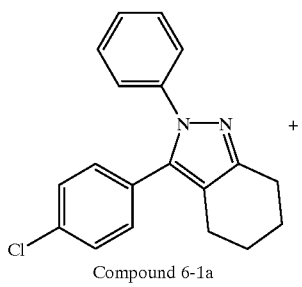

Compound 6-1a

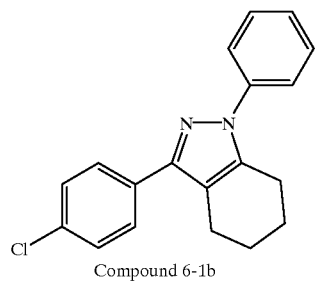

Compound 6-1b 3-(4-Chlorophenyl)-4,5,6,7-tetrahydro-2-phenyl-2H-indazole

Compound 6-1a 3-(4-Chlorophenyl)-4,5,6,7-tetrahydro-1-phenyl-1H-indazole

Compound 6-1b 2-(4-Chlorobenzoyl)cyclohexanone Compound 29c (946.8 g, 1 eq., 4.0 mMol) and phenylhydrazine (393.5 mg, 1 eq., 4.0 mMol) dissolved in CH₃OH (30 mL) were combined and refluxed for about 60 h. The reaction was monitored using TLC with 10% EtOAc/hexane. The product was chromatographed (1:3 EtOAc:hexane) to afford Compound 6-1a (77.0 mg); mp: 137–138° C. and Compound 6-1b (1.2 g); mp: 136–137° C. (97% total yield). Anal. Cald for Compound 6-1a, $C_{19}H_{17}ClN_2 \cdot 0.1H_2O$: C, 73.47; H, 5.58; N, 9.02. Found: C, 73.37; H, 5.65; N, 9.00. Anal. Cald for Compound 6-1b, $C_{19}H_{17}ClN_2$: C, 73.90; H, 5.55; N, 9.07. Found: C, 73.50; H, 5.52; N, 8.94.

EXAMPLE 7

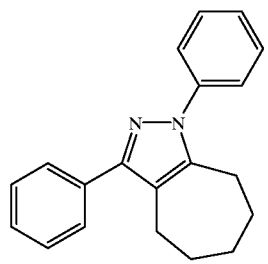

1,3-Diphenyl-4,5,6,7,8,-[5H]cycloheptano-[1,2-d]-pyrazole 0.20 Hydrate

Compound 7

To Compound 1-8 (280 mg, 0.965 mMol), tetrachloro-1,4-benzoquinone (475 mg, 1.93 mMol) in xylene (50 mL) was added using the procedure of Example 2. Compound 7 (240 mg, 86% yield) was obtained as a white solid; mp: 102–103° C. ¹H NMR (300 MHz, CDCl₃) δ 1.72 (m, 4H), 1.89 (m, 2H), 2.82 (m, 4H), 7.36–7.47 (m, 8H), 7.61 (d, 2H, J=9). CIMS m/e 289 (MH⁺). Anal. Cald for $C_{20}H_{20}N_2 \cdot 0.2H_2O$: C, 82.27; H, 7.04; N, 9.59. Found: C, 82.29; H, 6.87; N, 9.46.

EXAMPLE 8

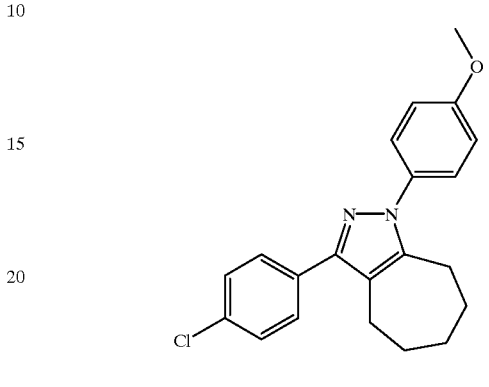

3-(4-Chlorophenyl)-1-(4-methoxyphenyl)-cycloheptano-[1,2-d]-pyrazole

Compound 8

A solution of 4-methoxyphenylhydrazine hydrochloride (349 mg, 2 mMol), Et₃N (0.2 g, 2 mMol) and 2-(4-chlorobenzoyl)-cycloheptan-1-one (501 mg, 2 mMol) in MeOH (25 mL) was stirred at about RT for about 24 h. The solvent was removed under reduced pressure; the resulting crude product was purified by column chromatography (silica gel, EtOAc:hexane). Compound 8 (80 mg, 11% yield) was obtained as a solid; mp: 131–132° C. ¹H NMR (300 MHz, CDCl₃) δ 1.71 (m, 4H), 1.88 (m, 2H), 2.63 (m, 4H), 3.85 (s, 3H), 6.97 (d, 2H, J=9), 7.34 (d, 2H, J=9), 7.38 (d, 2H, J=9), 7.53 (d, 2H, J=9). IR (KBr) cm⁻¹: 2917 (m), 2847 (m), 1515 (s), 1459 (s). CIMS m/e 352 (MH⁺). Anal. Cald for $C_{21}H_{21}ClN_2O$: C, 71.48; H, 6.00; N, 7.94. Found: C, 71.07; H, 5.99; N, 7.65.

EXAMPLE 9

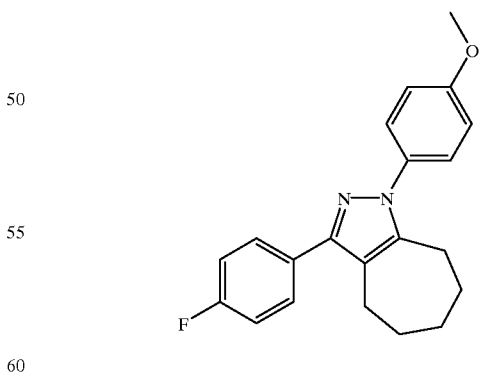

3-(4-Fluorophenyl)-1-(4-methoxyphenyl)-cycloheptano-[1,2-d]-pyrazole

Compound 9

From a mixture of 4-methoxyphenylhydrazine hydrochloride (349 mg, 2 mMol), Et₃N (0.2 g, 2 mMol) and 2-(4- fluorobenzoyl)-cycloheptan-1-one (468.5 mg, 2 mMol) in methanol (25 mL), Compound 9 (20 mg, 3% yield) was obtained as a solid; mp: 84–86° C. $^1$H NMR (300 MHz, CDCl$_3$) δ 1.69 (m, 4H), 1.72 (m, 2H), 2.75 (m, 2H), 3.85 (s, 3H), 6.97 (d, 2H, J=9), 7.09 (t, 2H, J=9), 7.34 (d, 2H, J=9), 7.55 (t, 2H, J=9). IR (KBr) cm$^{-1}$: 2933 (m), 2849 (m), 1514 (s), 1467 (s). CIMS m/e 337 (MH$^+$). Anal. Cald for C$_{21}$H$_{21}$FN$_2$O•0.4H$_2$O: C, 73.40; H, 6.39; N, 8.15. Found: C, 73.29; H, 6.06; N, 7.96.

EXAMPLE 10

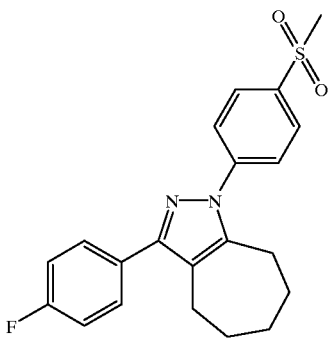

3-(4-Chlorophenyl)-1-(4-methylsulfonylphenyl)-cycloheptano-[1,2-d]-pyrazole

Compound 10

To a solution of 4-methylsulfonylphenylhydrazine (349 mg, 2 mMol) in glacial HOAc (10 mL) and DMSO (5 mL), 2-(4-chlorobenzoyl)-cycloheptan-1-one (501 mg, 2 mMol) was added. The resulting mixture was heated at about 100° C. for about 24 h. The solvent was removed under reduced pressure. The remaining residue was poured into icewater and extracted with EtOAc. The solvent was removed under reduced pressure and the crude product was chromatographed (silica gel, 1:1 EtOAc:hexane). Compound 10 (23 mg, 3% yield) was obtained as a solid; mp: 145–146.5° C. $^1$H NMR (300 MHz, CDCl$_3$) δ 1.86 (m, 4H), 1.91 (m, 2H), 2.73 (m, 2H), 2.89 (m, 2H), 3.12 (s, 3H), 7.40 (d, 2H, J 9), 7.52 (d, 2H, J=9), 7.68 (d, 2H, J=9), 8.08 (d, 2H, J=9). IR (KBr) cm$^{-1}$: 2927 (m), 2851 (w), 1594 (m), 1499 (m). CIMS m/e 401 (MH$^+$). Anal. Cald for C$_{21}$H$_{21}$ClN$_2$O$_2$S•0.2H$_2$O: C, 62.35; H, 5.33; N, 6.92. Found: C, 62.19; H, 5.14; N, 6.88.

EXAMPLE 11

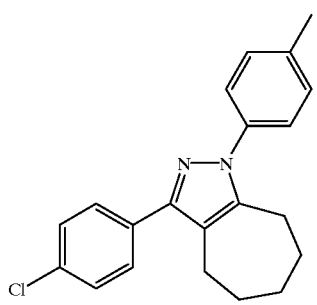

3-(4-Chlorophenyl)-1-(4-methylphenyl)-cycloheptano-[1,2-d]-pyrazole

Compound 11

From a mixture of 4-methylphenylhydrazine hydrochloride (317 mg, 2 mMol), Et$_3$N (0.2 g, 2 mMol) and 2-(4-chlorobenzoyl)-cycloheptan-1-one (501 mg, 2 mMol) in MeOH (25 mL), Compound 11 (170 mg, 25.4% yield) was obtained as a solid; mp: 143–144.5° C. $^1$H NMR (300 MHz, CDCl$_3$) δ 1.69 (m, 4H), 1.87 (m, 2H), 2.40 (s, 3H), 2.75 (m, 4H), 7.27 (d, 2H, J=9), 7.29 (d, 2H, J=9), 7.38 (d, 2H, J=9), 7.54 (d, 2H, J=9). IR (KBr) cm$^{-1}$: 2925 (m), 2850 (m), 1516 (s), 1508 (s). CIMS m/e 337 (MH$^+$). Anal. Cald for C$_{21}$H$_{21}$ClN$_2$•0.2H$_2$O: C, 74.08; H, 6.34; N, 8.23. Found: C, 73.89; H, 6.28; N, 8.13.

EXAMPLE 12

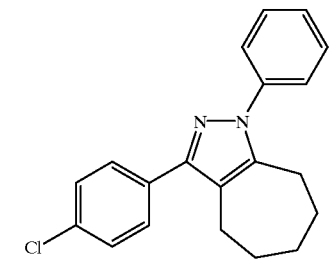

3-(4-Chlorophenyl)-1-phenyl-cycloheptano-[1,2-d]-pyrazole

Compound 12

From a mixture of phenylhydrazine (216 mg, 2 mMol) and 2-(4-chlorobenzoyl)-cycloheptan-1-one (501 mg, 2 mMol) in MeOH (25 mL), Compound 12 (117 mg, 18% yield) was obtained as a solid; mp 139–140° C. $^1$H NMR (300 MHz, CDCl$_3$) δ 1.72 (m, 4H), 1.89 (m, 2H), 2.74 (m, 2H), 2.80 (m, 2H), 7.37 (t, 1H, J=7), 7.39 (d, 2H, J=9), 7.45 (t, 2H, J=7), 7.47 (d, 2H, J=8), 7.55 (d, 2H, J=9). IR (KBr) cm$^{-1}$: 2925 (m), 2805 (m), 1595 (s), 1499 (s). CIMS m/e 323 (MH$^+$). Anal. Cald for C$_{20}$H$_{19}$ClN$_2$•0.1H$_2$O: C, 73.59; H, 5.99; N, 8.58. Found: C, 73.43; H, 5.70; N, 8.36.

EXAMPLE 13

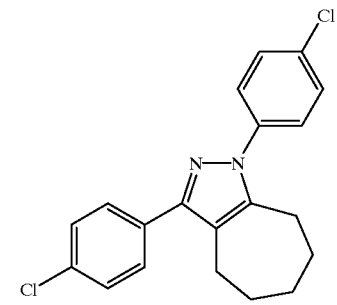

3-(4-Chlorophenyl)-1-(4-chlorophenyl)-cycloheptano-[1,2-d]-pyrazole

Compound 13

To a solution of 1,3-di-(4-chlorophenyl)-cis-3a,8a-octahydrocyclo-heptenapyrazole (200 mg, 0.56 mMol) in xylene (25 mL), tetrachloro-1,4-benzoquinone (273.7 mg, 1.12 mMol) was added. The resulting mixture was then refluxed for about 24 h and purified by chromatography (silica gel, EtOAc:hexane). Compound 13 (75 mg, 37.5% yield) was obtained as a solid; mp: 169–170.5° C. $^1$H NMR (300 MHz, CDCl₃) δ 1.73 (m, 4H), 1.89 (m, 2H), 2.75 (m, 2H), 2.80 (m, 2H), 6.97 (d, 2H, J=9), 7.40 (d, 2H, J=9), 7.45 (d, 2H, J=9), 7.52 (d, 2H, J=9). IR (KBr) cm⁻¹: 2921 (m), 2840 (m), 1689 (m), 1493 (s). CIMS m/e 357 (MH⁺). Anal. Cald for $C_{20}H_{18}Cl_2N\cdot0.2EtOAc$: C, 66.64; H, 5.27; N, 7.47. Found: C, 66.99; H, 5.69; N, 7.55.

EXAMPLE 13-1

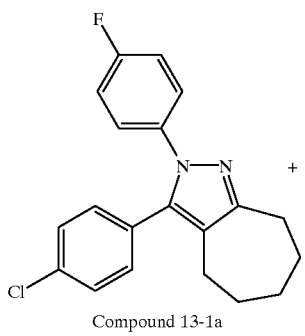

Compound 13-1a

+

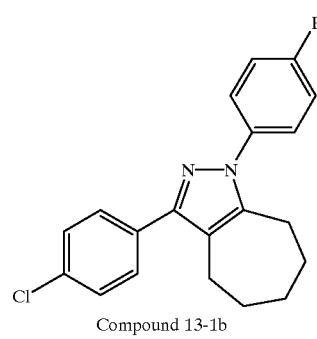

Compound 13-1b 3-(4-Chlorophenyl)-1-(4-fluorophenyl)-cycloheptano-[1,2-d]-pyrazole Compound 13-1b 2-(4-Chlorobenzoyl)cycloheptanone Compound 29d (1.003 g, 4.0 mMol), 4-Fluorophenylhydrazine•HCl (650.4 mg, 4.0 mMol) and Et₃N (0.404 g, 0.56 mL) were combined in CH₃OH (30 mL) and refluxed. The reaction was monitored by TLC with 10% EtOAc/hexane. The solvent was stripped off and the residue dissolved in toluene. The product was chromatographed with 1:3 EtOAc:hexane to afford Compound 13-1a (242.3 mg, 18% yield); mp: 154.5–156° C. and Compound 13-1b (858.2 mg, 63% yield) as a foam. Anal. Cald for Compound 13-1a, $C_{20}H_{18}ClFN_2$: C, 70.48; H, 5.32; N, 8.22. Found: C, 70.41; H, 5.39; N, 8.22. Anal. Cald for Compound 13-1b: C, 70.48; H, 5.32; N, 8.22. Found: C, 70.11; H, 5.38; N, 8.00.

Following the general procedure of Example 13-1, Compounds 13-1c, 13-1d, 13-1e, 13-1f, 13-1g and 13-1h set forth in Table 5a were prepared using appropriate reagents and starting materials.

TABLE 5a

| Ex# | Formula | R₁ | R₂ | Z₅ | Z₆ | Z₇ |
|---|---|---|---|---|---|---|
| 13-1c | 1 | 4-Cl | 4-Ome | CH₂CH₂ | CH₂ | CH₂ |
| 13-1d | 1 | 4-Cl | 4-SO₂Me | CH₂CH₂ | CH₂ | CH₂ |
| 13-1e | 1 | 4-Cl | 4-Me | CH₂CH₂ | CH₂ | CH₂ |
| 13-1f | 1 | 4-Cl | H | CH₂CH₂ | CH₂ | CH₂ |
| 13-1g | 1 | 4-F | 4-Ome | CH₂CH₂ | CH₂ | CH₂ |
| 13-1h | 1 | 4-F | 4-SO₂Me | CH₂CH₂ | CH₂ | CH₂ |

EXAMPLE 13-2

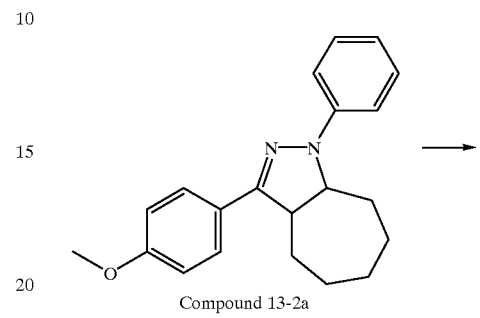

Compound 13-2a

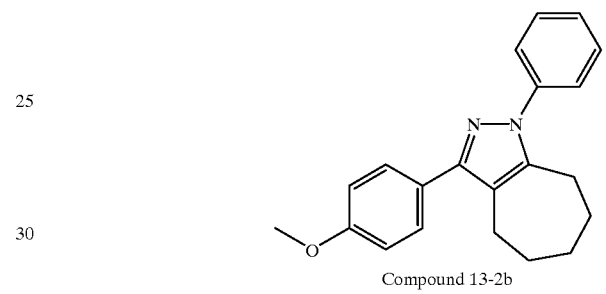

Compound 13-2b 3-(4-Methoxy)-1-phenyl-cycloheptano-[1,2-d]-pyrazole

Compound 13-2b

Compound 13-2a (480.66 mg, 1 eq., 1.5 mMol) and tetrachloro-1,4-benzoquinone (737.64 mg, 2 eq., 3 mMol) were combined in toluene (25 mL) and refluxed at about 110° C. for about 2.5 h. The reaction was monitored by TLC with 10% EtOAc/hexane, then the solid was filtered off and a half volume of hexane was added. The product was chromatographed using 10% EtOAc/hexane to afford Compound 13-2b (270 mg, 56.6% yield); mp: 119–120° C. Anal. Cald for Compound 13-2b, $C_{21}H_{22}N_2O$: C, 79.21; H, 6.96; N, 8.80. Found: C, 78.89; H, 6.92; N, 8.68.

EXAMPLE 14

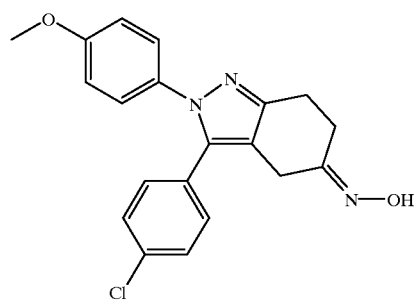

syn and anti-3-(4-Chlorophenyl)-5-hydroxyimino-2-(4-methoxyphenyl)-4,5,6,7-tetrahydro-2H-indazole Compound 14

Compound 31 (1.2 g, 3.4 mL), hydroxylamine hydrochloride (1.7 g, 24 mL) and NaOAc (1.7 g, 21 mL) in 100 mL of ethanol were combined in a 200 mL round bottom flask and stirred under nitrogen. The course of the reaction was followed by TLC in ether with iodine visualization. After the ethanol was evaporated, the residue was partitioned between 100 mL of water and 200 mL of ether. The ether layer was dried over anhydrous sodium sulfate, filtered through Celite and concentrated. The crude product (0.90 g, 72% yield) was then chromatographed on 100 g of silica and eluted with ether to afford the combined oxime Compound 14 (0.60 g, 48% yield) as a white solid, mp: 165–170° C., (ca. 5:1 syn-oxime:anti-oxime). A 3.0 g portion of the oxime mixture was obtained in the same manner on a larger scale, then chromatographed on 400 g of silica and eluted with 3:1 ethyl acetate:hexane to afford the syn-oxime Compound 14 (0.28 g, 9.3% yield) (Rf=0.651), mp: 168–171° C.; and the anti-oxime Compound 14 (2.6 g, 87% yield) (Rf=0.48); mp: 158–160.0° C.

Syn-oxime $^1$H NMR (300 MHz, CDCl$_3$): 82.95 (m, 5H), 3.4 (s, 1H), 3.8 (s, 1H), 6.8 (d, 2H, J=7), 7.15 (q, 4H, J=8); 7.35 (d, 2H, J=7). IR (KBr) cm$^{-1}$: 3200, 3195, 1598, 1250. CIMS m/e 368 (MH$^+$). Anal. Calcd for $C_{20}H_{18}ClN_3O_2$: C, 65.31; H, 4.93; N, 11.42. Found: C, 65.28; H, 4.97; N, 11.28.

Anti-oxime $^1$H NMR (300 MHz, CDCl$_3$): 82.8 (2m, 1H), 3.85 (s, 1H), 6.8 (d, 2H, J=7), 7.15 (q, 4H, J=8); 7.3 (d, 2H, J=7). IR (KBr) cm$^{-1}$: 1517, 1250, 830. CIMS m/e 368 (MH$^+$). Anal. Calcd. for $C_{20}H_{18}ClN_3O_2 \cdot \frac{1}{4}H_2O$: C, 64.52; H, 5.01; N, 1129. Found: C, 64.60; H, 4.94; N, 11.16.

EXAMPLE 15

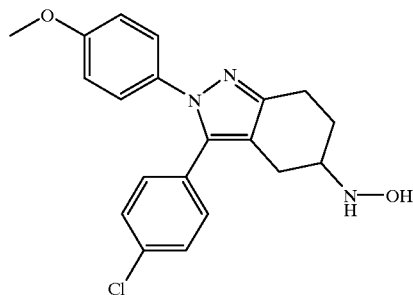

3-(4-Chlorophenyl)-4,5,6,7-tetrahydro-5-hydroxylamino-2-(4-methoxyphenyl)-2H-indazole ¼ Hydrate Compound 15

The oxime Compound 14 (10.08 g, 27.4 mMol) and 150 mL of MeOH with a methyl orange indicator were added to a round bottom flask. The mixture was stirred under N$_2$ at about RT and treated with a solution of NaCNBH$_3$ (5.30 g, 2 eq., 84.3 mMol) in MeOH (15 mL) and a solution of HCl (10 mL) in MeOH (30 mL). The reaction was monitored by TLC in EtOAc with UV visualization. After about 2 h, the mixture was quenched with 50 mL H$_2$O and extracted with 3×50 mL EtOAc. The ethyl acetate layer was dried over anhydrous Na$_2$SO$_4$, then filtered through Celite and concentrated to a yellow solid (9.01 g, 89% yield). The crude material (8.7 g) was purified by column chromatography on 900 g of silica, eluted with EtOAc to afford Compound 15 (1.96 g, 42% yield) as a white solid, (Rf=0.15), mp:

122–125° C. $^1$H NMR (300 MHz, CDCl$_3$): 52.2 (br m, 1H), 2.55 (q, 2H), 2.85 (q, 2H), 2.95 (m, 2H), 3.4 (br s, 1H), 3.8 (s, 1H), 6.8 (d, 2H, J=9), 7.1 (q, 4H, J=9), 7.27 (d, 2H, J=9). IR (KBr) cm$^{-1}$: 3235, 2900, 1500, 300. CIMS m/e 370 (MH$^+$). Anal. Calcd. for $C_{20}H_{20}ClN_3O_2 \cdot \frac{1}{4}H_2O$: C, 64.17; H, 5.52; N, 11.22. Found: C, 64.07; H, 5.34; N, 11.24.

EXAMPLE 16

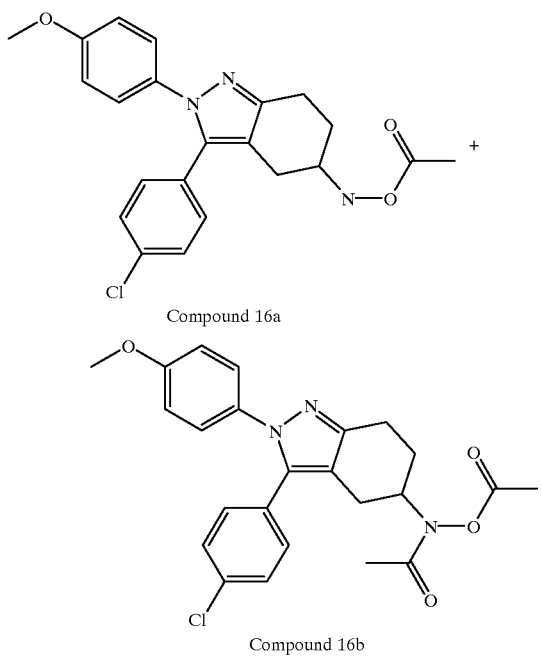

5-(O-Acetylhydroxylamino)-3-(4-chlorophenyl)-4,5,6,7-tetrahydro-2-(4-methoxyphenyl)-2H-indazole Hemihydrate Compound 16a 5-(N,O-Diacetylhydroxylamino)-3-(4-chlorophenyl)-4,5,6,7-tetrahydro-2-(4-methoxyphenyl)-2H-indazole Compound 16b Hydroxylamine Compound 15 (1.0 g, 2.7 mMol), methylene chloride (20 mL) and triethylamine (0.38 mL, 1 eq.) were added to a round bottom flask and stirred under N$_2$ at about 0° C., then treated slowly with acetic anhydride (0.26 mL, 1 eq.) in CH$_2$Cl$_2$ (5 mL) and allowed to warm to about RT. The reaction was monitored by TLC in 3:1 EtOAc:hexane with UV light and iodine visualization. After about 1 h, the mixture was quenched with 50 mL of H$_2$O and extracted with 3×20 mL of ether. The ether layer was dried over anhydrous Na$_2$SO$_4$, filtered through Celite and concentrated to an oil (0.95 g, 88%). The crude material was purified by column chromatography on 100 g of silica, eluted with 3:1 EtOAc:hexane to afford Compound 16a (0.39 g, 41% yield) as a white solid, (Rf=0.39); mp: 107–110° C. and the ¼ and ⅓ hydrate of Compound 16b (0.17 g, 18% yield) as an off-white solid, (Rf=0.31), mp: 95–97° C.

Hemihydrate $^1$H NMR (300 MHz, CDCl$_3$): 82.2 (s, 3H), 2.5 (d, 1H, J=8), 2.6 (d, 1H, J=8), 2.9–3.0 (m, 2H), 3.0–3.1 (m, 1H), 3.4

(br s, 1H), 3.8 (s, 3H), 6.8 (d, 2H, J=9), 7.1 (q, 4H, J=8), 7.3 (d, 21H, J=8 Hz), 7.65 (d, 1H, J=8 Hz). IR (KBr) cm$^{-1}$: 1738, 1517. CIMS m/e 411 (MH$^+$). Anal. Calcd. for $C_{22}H_{22}ClN_3O_3 \cdot \frac{1}{2}H_2O$: C, 62.78; H, 5.51; N, 9.98. Found: C, 63.16; H, 5.36; N, 9.73.

¼ Hydrate $^1$H NMR (300 MHz, CDCl$_3$): 82.1 (br s, 3H), 2.2 (s, 3H), 2.6–3.1 (m, 4H), 3.8 (s, 3H), 6.8 (d, 2H, J=8), 7.1 (q, 4H, J=7), 7.3 (d, 2H, J=8). IR (KBr) cm$^{-1}$: 1798, 1675, 1517, 1250, 1178. CIMS m/e 454 (MH$^+$). Anal. Calcd. for $C_{24}H_{24}ClN_3O_4 \cdot \frac{1}{4}H_2O$: C, 62.88; H, 5.39; N, 9.17. Found C, 62.94; H, 5.29; N, 8.98.

⅓ Hydrate $^1$H NMR (300 MHz, CDCl$_3$): 82.1 (s, 3H), 2.2 (s, 3H), 2.8 (m, 4H), 3.8 (s, 3H), 6.8 (d, 2H, J=8), 7.1 (q, 4H, J=7), 7.3 (d, 2H, J=8). Anal. Calcd. for $C_{24}H_{24}ClN_3O_4 \cdot \frac{1}{3}H_2O$: C, 62.68; H, 5.67; N, 9.13. Found C, 62.54; H, 5.53; N, 8.73.

EXAMPLE 17

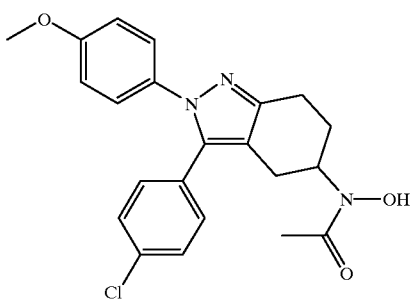

5-(N-Acetylhydroxyamino)-3-(4-chlorophenyl)-4,5,6,7-tetrahydro-2-(4-methoxyphenyl)-2H-indazole ⅒ Hydrate Compound 17

The diacetyl Compound 16b (0.70g, 1.5 mMol) and 10 mL of IPA were combined in a round bottom flask and a solution of LiOH (0.14 mg) in 20 mL:1 mL IPA:H$_2$O was added. The mixture was stirred under N$_2$ for about 2 h and monitored by TLC in 3:1 CH$_2$Cl$_2$:MeOH with UV visualization. When completed, the reaction was quenched with 30 mL water and extracted with 3×30 mL methylene chloride. The organic layer was dried over anhydrous Na$_2$SO$_4$, filtered over Celite then concentrated and purified by column chromatography on 100 g of silica. The product was eluted using 3:1 CH$_2$Cl$_2$:MeOH and recrystallized in ether to afford Compound 17 (0.23 g, 36% yield) (Rf=0.52); mp: 196–198° C. $^1$H NMR (300 MHz, CDCl$_3$): 52.15 (s, 31-11), 2.6 (q, 21-11), 2.8 (bm, 2H), 3.8 (s, 31-1), 4.2 (bs, 1H), 6.8 (d, 2H, J=8), 7.1 (q, 41-11, J=8), 7.3 (d, 2H, J=8). IR (KBr) cm$^{-1}$: 3100, 2900, 1600, 1500. CIMS m/e 412 (MH$^+$). Anal. Calcd. for $C_{22}H_{22}ClN_3O_3 \cdot 0.1H_2O$: C, 63.87; H, 5.41; N, 10.16. Found C, 63.71; H, 5.47; N, 9.87.

EXAMPLE 18

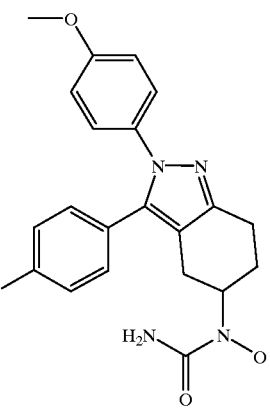

N-[3-(4-Chlorophenyl)-4,5,6,7-tetrahydro-2-(4-methoxyphenyl)-2H-indazol-5-yl]hydroxyurea, ¼ Hydrate Compound 18

Hydroxylamine Compound 15 (1.5 g, 4 mMol), THF (20 mL) and trimethylsilylisocyanate (15 mL) were added to a round bottom flask and stirred under N$_2$ while heating to reflux. The reaction was monitored by TLC in 9:1 methylene chloride:methanol and stirring was continued overnight. The mixture was concentrated, then MeOH (35 mL) was added to the flask and the reaction was heated to reflux for about 1 h. The mixture was then filtered to afford Compound 18 (1.04 g, 62% yield) as a white solid, (Rf=0.21); mp: 190–194° C. $^1$H NMR (300 MHz, CDCl$_3$): 81.82 (m, 2H), 2.3 (2d, 2H), 2.6 (m, 2H), 3.5 (s, 3H), 4.16 (bm, 1H), 5.4 (bs, 2H), 6.5 (d, 2H, J=7), 6.8 (q, 4H, J=7), 6.9 (d, 2H, J=7), 8.7 (s, 1H). IR (KBr) cm$^{-1}$: 3100, 2800, 1655, 1518. CIMS m/e 413 (MH$^+$). Anal. Calcd. for $C_{21}H_{21}ClN_4O_3 \cdot \frac{1}{4}H_2O$: C, 60.43; H, 5.19; N, 13.42. Found C, 60.34: H, 5.06: N, 13.28.

EXAMPLE 19

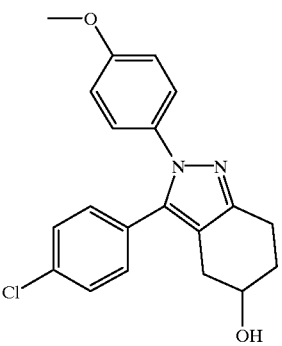

3-(4-Chlorophenyl)-4,5,6,7-tetrahydro-5-hydroxy-2-(4-methoxyphenyl)-2H-indazole

Compound 19

The o-methoxychloroketone Compound 31 (R$_2$=OMe, R$_1$=Cl) (2.06 g, 5.80 mMol) and 30 mL of THF were added to a round bottomed flask under N$_2$. Dibal (8.7 mL) was slowly added while the reaction was stirred over ice. The reaction was complete after about 1 h and then concentrated on a rotary evaporator. H$_2$O (100 mL) was added to the solid and then extracted with a mixture of ether and ethyl acetate. The organic layer was dried over anhydrous Na$_2$SO$_4$, filtered over Celite and concentrated. The crude material was purified by column chromatography on 200 g of silica, eluted with EtOAc and recrystallized with ether/hexane to afford Compound 19 (1.52 g, 73% yield) as a white solid, (Rf= 0.15), mp: 95–98° C. $^1$H NMR (300 MHz, CDCl$_3$): 82.1 (m, 1H), 2.6 (q, 2H), 2.9 (m, 2H), 3.05 (m, 2H), 3.8 (s, 3H), 4.2 (bs, 1H), 6.8 (d, 2H, J=9), 7.25(q, 4H, J=9), 7.29 (d, 2H, J=9). IR (KBr) cm$^{-1}$: 3500, 3000, 2400, 1600. CIMS m/e 355 (MH$^+$). Anal. Calcd. for C$_{20}$H$_{19}$ClN$_2$O$_2$: C, 67.70; H, 5.40; N, 7.89. Found C, 67.42; H, 5.11; N, 7.97.

EXAMPLE 20

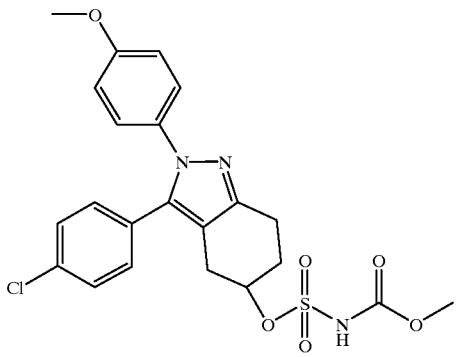

3-(4-Chlorophenyl)-4,5,6,7-tetrahydro-5-(methoxycarbonylsulfamoyloxy)-2-(4-methoxyphenyl)-2H-indazole Compound 20

The o-methoxychloroketone Compound 31 (R$_2$=OMe, R$_1$=Cl) (0.35 g, 1 mMol), 20 mL of benzene and Burgess Reagent (0.29 g, 1.2 mMol) were added to a round bottom flask and stirred under N$_2$ while heating to reflux. The reaction was monitored by TLC in EtOAc with UV visualization. After about 1.5 h, the reaction was quenched with 100 mL H$_2$O. The flask was washed with benzene to ensure all of the material was collected. The benzene layer was dried over anhydrous Na$_2$SO$_4$, filtered over Celite and concentrated to yield 100 mg of a mixture of isomers of the conjugated ring. The aqueous layer was acidified with 250 mL 3N HCl and filtered to produce Compound 20 (0.260 g, 78% yield) as a white solid, (Rf=0.259), mp: 142–148° C. $^1$H NMR (300 MHz, CDCl$_3$): 52.1–2.5, (2m, 3H), 2.95 (m, 4H), 3.77(s, 3H), 3.79 (s, 3H), 5.3 (bs, 1H), 6.8 (d, 2H, J=9), 7.25 (q, 4H, J=9), 7.36 (d, 2H, J=9). IR (KBr) cm$^{-1}$: 2800, 1600, 1570. CIMS m/e 491 (MH$^+$). Anal. Calcd. for C$_{22}$H$_{22}$ClN$_3$O$_6$S: C, 53.77; H, 4.51; N, 8.55. Found C, 54.14; H, 4.31; N, 8.11.

EXAMPLE 21

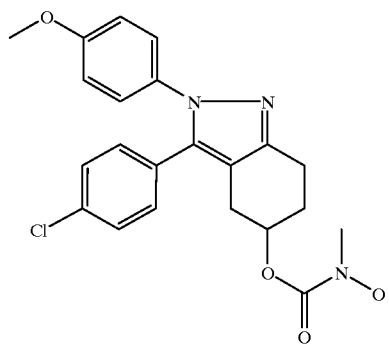

3-(4-Chlorophenyl)-4,5,6,7-tetrahydro-2-(4-methoxyphenyl)-5-(N-hydroxy-N-methylcarbamoyloxy)-2H-indazole ¼ Ether Compound 21

Compound 19 (1.0 g, 2.8 mMol), triphosgene (0.42 g, 1.4 mMol) and pyridine (0.22 mL, 2.8 mMol) were combined in dichloromethane (20 mL) at about 0° C. for about 15 min. The reaction was left overnight at about RT and was concentrated to afford a crude chloroformate intermediate (1.77 g) that was used without purification in the next immediate step.

Methyl hydroxylamine hydrochloride (1.42 g, 4 eq.) and triethylamine (2.2 mL) in CH$_2$Cl$_2$ (10 mL) were combined in a round bottom flask and stirred at about 0° C. To this mixture, a solution of the chloroformate intermediate in CH$_2$Cl$_2$ (25 mL) was added. The mixture was stirred at about 0° C. for about 20 minutes, then removed from the ice bath and stirred at about RT overnight. The mixture was quenched with H$_2$O (100 mL) and extracted with 3×100 mL EtOAc. The organic layers were dried and filtered through Celite. The crude product was purified by column chromatography on 150 g silica, eluted with EtOAc to afford Compound 21 (0.076 g, 6% yield) as a yellow foam (Rf= 0.44). $^1$H NMR (300 MHz, CDCl$_3$): 82.1 (m, 2H), 2.5–3.1 (m, 4H, indazole ring), 3.15 (s, 3H, Me), 3.79, (s, 3H, Me), 6.8 (dd, 2H, ar), 7.05–7.11, (q, 4H, ar), 7.29 (dd, 2H, ar). IR (KBr) cm$^{-1}$: 1 2900, 1696,1516. CIMS m/e 428 (MH+). Anal. Calcd. for C$_{22}$H$_{22}$ClN$_3$O$_4$•¼Et$_2$O: C, 61.88; H, 5.53; N, 9.41. Found: C, 62.20; H, 5.53; N, 9.23.

EXAMPLE 22

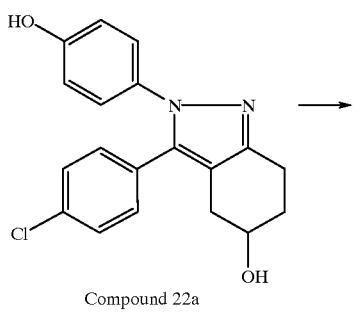

Compound 22a

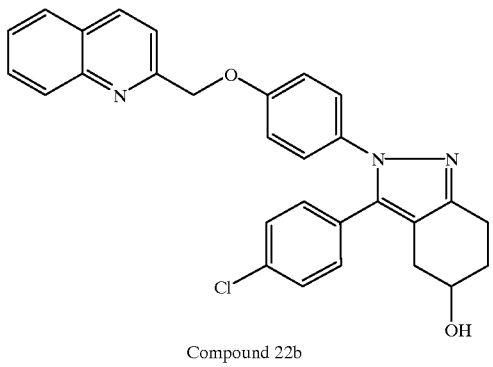

Compound 22b

N-[3-(4-Chlorophenyl)-4,5,6,7-tetrahydro-5-hydroxy-2-[4-(2-quinolyl)methoxyphenyl])-2H-indazole 0.75 Hydrate

Compound 22b

Compound 19 (1.00 g, 2.82 mMol) was heated to reflux overnight in 48% HBr. $H_2O$ (100 mL) was added and the mixture was extracted with EtOAc (3×50 mL). The extract was dried over sodium sulfate, filtered through Celite and concentrated to a white solid. The crude material was recrystallized from ether to afford the hydroxy phenol intermediate Compound 22a (0.53 g, 55% yield) ($R_1$=Cl, $R_2$=OH). A portion of the intermediate Compound 22a (0.40 g, 1.2 mMol), potassium carbonate (0.44 g, 2.35 mMol) and 2-(chloromethyl)quinoline hydrochloride (0.54 g, 2.34 mMol) in acetone (20 mL) were combined in a round bottom flask and heated to reflux for about 48 h. The mixture was concentrated, taken up in $H_2O$ (150 mL) and extracted using 2×100 mL EtOAc. The organic layer was dried, filtered and concentrated to obtain a red oil that was purified by column chromatography, eluted in 9:1 $CH_2Cl_2$:MeOH and then crystallized in EtOAc/$Et_2O$ to afford Compound 22b (0.280 g, 48% yield) as a white solid, (Rf=0.44), mp: 124–126° C. $^1H$ NMR (300 MHz, $CDCl_3$): 52.02 (m, 2H, $CH_2$), 2.6 (dd, 1H, CH), 2.9 (m, 2H, $CH_2$), 2.97 (m, 2H, $CH_2$), 4.2 (bs, 1H, OH), 5.36 (s, 2H, $CH_2$), 6.9 (d, 2H, J=9), 7.1 (dd, 4H, J=9), 7.2 (d, 2H, J=8), 7.5 (t, 1H, Quin, J=7), 7.6 (d, 1H), 7.7 (t, 1H), 7.8 (d, 1H), 8.05 (d, 1H), 8.2 (d, 2H). IR (KBr) $cm^{-1}$: 3400,1500, 1246,1050. CIMS m/e 482 ($MH^+$). Anal Calc. for $C_{29}H_{24}ClN_3O_2 \cdot 0.75H_2O$: C, 70.30; H, 5.19; N, 8.48. Found: C, 70.12; H, 4.98; N, 8.48.

EXAMPLE 23

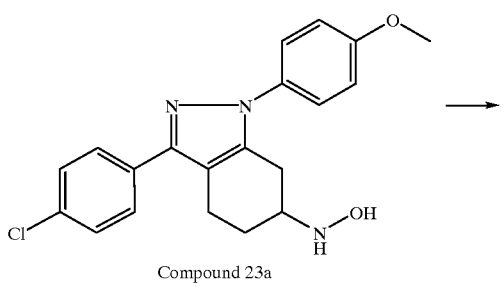

Compound 23a

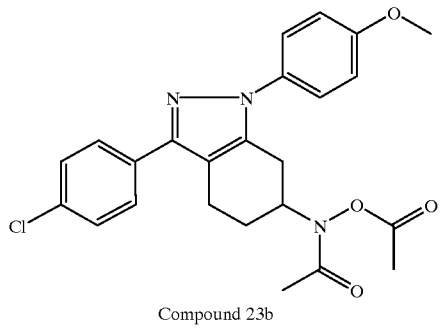

Compound 23b

6-(N,O-Diacetylhydroxylamino)-3-(4-chlorophenyl)-4,5,6,7-tetrahydro-1-(4-methoxyphenyl)-1H-indazole

Compound 23b

The hydroxylamine 6-(hydroxyamino)-3-(4-chlorophenyl)-4,5,6,7-tetrahydro-1-(4-methoxyphenyl)-1H-indazole Compound 23a (1.0 g, 2.7 mMol) and methylene chloride (25 mL) were added to a round bottom flask. To this was added a mixture of $AC_2O$ (0.255 mL, 2.2 eq.) in methylene chloride (10 mL). The reaction was stirred down to about 0° C. under $N_2$, then warmed to about RT and monitored by TLC in ethyl acetate and visualized by UV. Additional $AC_2O$ (2.2 eq.) was added and the mixture was stirred for about an additional 2 h. The reaction mixture was quenched with water (50 mL) and extracted with ether (3×25 mL). The ether layer was dried over anhydrous $Na_2SO_4$, filtered over Celite and concentrated to a crude product (1.71 g). The product was purified by column chromatography on 200 g of silica and eluted with ethyl acetate to afford Compound 23b (0.80 g, 69% yield) as a white solid; (Rf=0.64), mp: 176–177° C. $^1H$ NMR (300 MHz, $CDCl_3$) δ 1.8–2.2 (m, 2H), 2.0 (s, 3H), 2.2 (s, 3H), 2.9 (m, 4H), 3.8 (s, 3H), 4.9 (bs, 1H), 7.0 (d, 2H, J=9), 7.35 (q, 4H, J=9), 7.7 (d, 2H, J=9). IR (KBr) $cm^{-1}$: 2360, 2340,1794, 1684, 1550. CIMS m/e 454 ($MH^+$). Anal. Calcd. for $C_{24}H_{24}ClN_3O_4$: C, 63.53; H, 5.30; N, 9.25. Found C, 63.30; H, 5.21; N, 9.19.

EXAMPLE 24

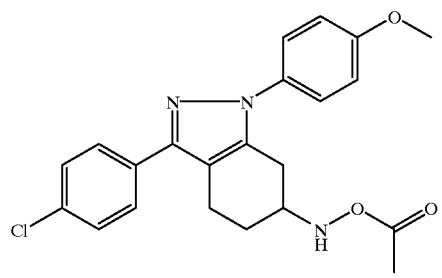

6-(O-Acetylhydroxylamino)-3-(4-chlorophenyl)-4,5,6,7-tetrahydro-1-(4-methoxyphenyl)-1H-indazole Hemihydrate

Compound 24

The hydroxylamine Compound 23a (0.50 g, 1.35 mMol), 10 mL of methylene chloride and $(C_2H_5)_3N$ (0.19 mL, 1 eq.)

were added to a round bottom flask and stirred at about 0° C. To this was added a mixture of $Ac_2O$ (0.13 mL, 1.0 eq.) in methylene chloride (10 mL). The reaction was stirred under $N_2$ while being warmed to about RT and monitored by TLC in 3:1 ethyl acetate:hexane using UV visualization. A solvent system of 50:50 ethyl acetate:hexane demonstrated better separation. The reaction was completed after about 0.5 h, then quenched with water (50 mL) and extracted with ether (3×25 mL). The ether layer was dried over anhydrous $Na_2SO_4$, filtered over Celite and concentrated to 0.82 g of crude material. The material was purified by column chromatography on 100 g of silica and eluted with a 50:50 mixture of ethyl acetate:hexane to afford Compound 24 (0.19 g, 84% yield) as an oil. The oil was crystallized in ether/hexane to give a white solid (Rf=0.64), mp: 83–84° C. $^1$H NMR (300 MHz, $CDCl_3$) δ 1.85 (m, 2H), 2.7 (m, 2H), 2.9 (m, 2H), 3.45 (bs, 1H), 3.9 (s, 3H), 7.0 (d, 2H, J=8), 7.4 (q, 4H, J=8), 7.7 (d, 2H, J=8). IR (KBr) $cm^{-1}$: 2360, 2330, 1550. CIMS m/e 412 ($MH^+$). Anal. Calc. for $C_{22}H_{22}ClN_3O_3\cdot 0.5H_2O$: C, 62.78; H, 5.51; N, 9.98. Found: C, 62.35; H, 5.24; N, 10.24.

EXAMPLE 25

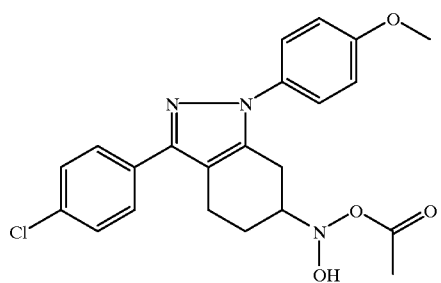

6-(N-Acetylhydroxylamino)-3-(4-chlorophenyl)-4,5,6,7-tetrahydro-1-(4-methoxyphenyl)-1H-indazole Hemihydrate Compound 25

The 1,4 diacetyl isomer Compound 23b (0.42 g, 0.93 mMol) and IPA (10 mL) were combined in a round bottom flask and a solution of LiOH (0.08 mg) in 20 mL IPA:1 mL $H_2O$ was added. The mixture was stirred under $N_2$ for about 2 h and monitored by TLC in 3:1 ethyl acetate:hexane using UV visualization. When completed, the reaction was quenched with water (30 mL) and extracted with methylene chloride (3×30 mL). The organic layer was dried over anhydrous $Na_2SO_4$, filtered over Celite and concentrated to obtain a crude yield of 0.52 g. The material was purified by column chromatography on 100 g of silica, eluted with a 3:1 ethyl acetate:hexane solution to afford Compound 25 (0.13 g, 34% yield) (Rf=0.37), mp: 189–191° C. The product was recrystallized in ether. $^1$H NMR (300 MHz, $CDCl_3$) δ 2.15 (s, 3H), 2.3 (bm, 2H), 2.8 (q, 2H), 2.95 (m, 2H), 3.4 (m, 1H), 3.85 (s, 3H), 7.0 (d, 2H, J=8), 7.4 (q, 4H, J=8), 7.75 (d, 2H, J=8). IR (KBr) $cm^{-1}$: 3100, 2900, 1600, 1500. CIMS m/e 412 ($MH^+$). Anal. Calcd. for $C_{22}H_{22}ClN_3O_3\cdot 0.5H_2O$: C, 62.78; H, 5.51; N, 9.98. Found: C, 62.49; H, 5.18; N, 9.80.

EXAMPLE 25-1

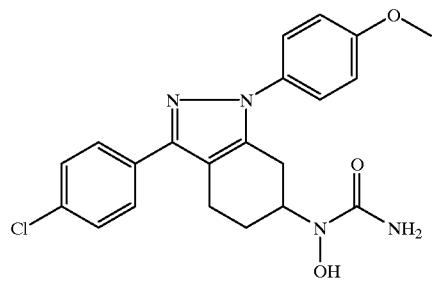

N-[1-(4-Chlorophenyl)-4,5,6,7-tetrahydro-1-(4-methoxyphenyl)-1H-indazol-6-yl]hydroxyurea, 0.2 Hydrate, 0.5 THF Compound 25-1

Hydroxylamine Compound 23a (1.0 g, 2.7 mMol), THF (20 mL) and trimethylsilylisocyanate (10 mL) were combined in a round bottom flask, then heated to reflux under $N_2$ for about 1 h and cooled to about RT. The product was filtered and washed with ether to afford Compound 25-1 (0.41 g) as a white solid. A second and third crystallization afforded additional product (0.65 g, 94% total yield); mp: 195–197° C. $^1$H NMR (300 MHz, $CDCl_3$) δ 1.8 (bt, 2H, $CH_2$), 2.6 (d, 1H, CH), 2.9 (bt, 2H, $CH_2$), 3.0 (t, 1H, CH), 3.8 (s, 3H, OMe), 6.4 (s, 2H, $NH_2$), 6.4 (s, 2H, aromatic), 7.5 (q, 4H, aromatic), 7.8 (9d, 2H, aromatic), 9.2 (s, 1H, OH). IR (KBr) $cm^{-1}$: 3400, 3100, 1650, 1550. CIMS m/e 413 ($MH^+$). Anal. Calcd. for $C_{21}H_{21}ClN_4O_3\cdot 0.2H_2O\cdot 0.5THF$: C, 61.05; H, 5.66, N, 12.38. Found C, 60.85: H, 5.57: N, 12.14.

EXAMPLE 26

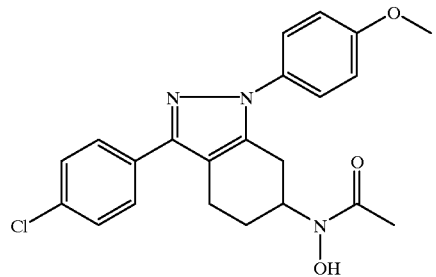

6-(N-Acetylhydroxylamino)-3-(4-chlorophenyl)-4,5,6,7-tetrahydro-1-(4-methoxyphenyl)-1H-indazole ⅓ Hydrate Compound 26

A hydroxylamine compound having Formula 2 prepared using the procedure of Example 15 ($R_1$=Cl, $R_2$=OMe) (0.72 g, 1.9 mMol) and $CH_2Cl_2$ (30 mL) were combined in a round bottom flask and a solution of $Ac_2O$ (0.37 mL) in $CH_2Cl_2$ (10 mL) was added. The mixture was stirred under $N_2$ for about 0.5 h and monitored by TLC in ethyl acetate using UV visualization. When completed, the reaction was quenched with 50 mL water and extracted with 3×30 mL ether. The organic layer was dried over anhydrous $Na_2SO_4$ and filtered over Celite, then concentrated and purified by column chromatography on 120 g of silica, eluted with ethyl acetate to afford Compound 26 (0.112 g, 13% yield) (Rf=0.36), mp: 124–129° C. $^1$H NMR (300 MHz, $CDCl_3$): $\delta$2.15 (s, 3H), 2.3 (bm, 2H), 2.8 (q, 2H), 2.95 (m, 2H), 3.4 (m, 1H), 3.85 (s, 3H), 7.0 (d, 2H, J=8), 7.4 (q, 4H, J=8), 7.75 (d, 2H, J=8). IR (KBr) $cm^{-1}$: 3100, 2900,1600,1500. CIMS m/e 412 ($MH^+$). Anal. Calcd. for $C_{22}H_{22}ClN_3O_3 \cdot \frac{1}{3}H_2O$: C, 63.23; H, 5.31; N, 10.05. Found: C, 63.44; H, 5.30; N, 9.92.

EXAMPLE 27

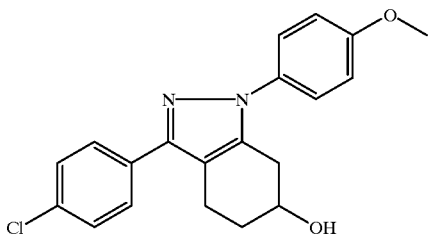

3-(4-Chlorophenyl)-4,5,6,7-tetrahydro-6-hydroxy-1-(4-methoxyphenyl)-1H-indazole

Compound 27

A 1,4-isomer of the ketone Compound 31 (where $R_1$=Cl and $R_2$=OMe) (2.00 g, 5.70 mMol) and 30 mL of THF were added to a round bottomed flask under $N_2$, then Dibal (9.9 mL) was slowly added while the reaction was stirred over ice. The reaction was completed after about 2 h then concentrated on the rotary evaporator. $H_2O$ (100 mL) was added to the solid and then extracted with ethyl acetate. The organic layer was dried over anhydrous $Na_2SO_4$, filtered over Celite and concentrated. The crude material was purified with ether recrystallization to afford Compound 27 (1.60 g, 79.6% yield) as a white solid; (Rf=0.379), mp: 162–164° C. $^1$H NMR (300 MHz, $CDCl_3$): $\delta$2.1 (m, 1H), 2.7 (q, 2H), 2.9 (m, 2H), 3.05 (m, 2H), 3.8 (s, 3H), 4.2 (bs, 1H), 6.95 (d, 2H, J=9), 7.4 (q, 4H, J=9), 7.75 (d, 2H, J=9). IR (KBr) $cm^{-1}$: 3400, 2900, 2300, 1550. CIMS m/e 355 ($MH^+$). Anal. Calcd. for $C_{20}H_{19}ClN_2O_2$: C, 67.70; H, 5.39; N, 7.89. Found C, 67.33; H, 5.39; N, 7.79.

EXAMPLE 28

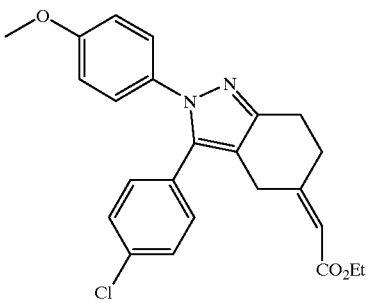

Ethyl-(Z)-3-(4-Chlorophenyl)-4,5,6,7-tetrahydro-2-(4-methoxyphenyl)-5-2H indazolylideneacetate Compound 28

NaH in an oil dispersion was added to a round bottom flask and washed with hexane and THF (20 mL) to remove the oil. Triethylphosphonoacetate (1.09 mL neat, 5.5 mMol) was added while the reaction was stirred at about 0° C. under $N_2$. The mixture was then treated with the ketone Compound 31 (2.17 g, 6 mMol) in THF (10 mL) and stirred for about an additional 30 min when a color change from orange to green was observed. The reaction was quenched with $NH_4Cl$ (50 mL) and extracted with 3×200 mL of $Et_2O$ (a color change from green to orange was observed). The organic layers were dried, filtered over Celite and concentrated. The crude product was purified by column chromatography on 300 g silica in 6:4 hexane:ethyl acetate to afford Compound 28 (0.67 g, 26% yield) as a yellow solid; (Rf=0.395), mp: 142–145° C. $^1$H NMR (300 MHz, $CDCl_3$): $\delta$1.5 (t, 3H, Me), 2.67 (t, 2H, $CH_2$), 2.9 (t, 2H, $CH_2$), 3.8 (s, 3H, Me), 4.05, (s, 2H, $CH_2$), 4.15 (q, 2H, $CH_2$), 6.8 (d, 2H, ar, J=9), 7.15 (m, 4H, ar), 7.3 (d, 2H, ar, J=8.5). IR (KBr) $cm^{-1}$: 2900,1700, 1500. CIMS m/e 423 ($MH^+$). Anal. Calcd. for $C_{24}H_{23}ClN_2O_3$: C, 68.16; H, 5.48; N, 6.62. Found:C, 67.94; H, 5.55; N, 6.51.

EXAMPLE 29

Compound 29a

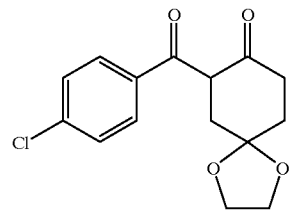

7-(4-Chlorobenzoyl)-8-oxo-1,4-dioxaspiro[4,5]decane

Compound 29a

Cyclohexane-1,4-dione-monoethylene glycol ketal (93.12 g, 20 mMol) was added to a solution of lithium hexamethyldisilazide (20 mMol) in THF (100 mL) at about −78° C. over about a 10 min period. After about 1 h, the solution was transferred via canula to a solution of 4-chlorobenzoyl chloride (3.50 g, 20 mMol) in THF (50 mL) at about −78° C. over about a 15 min period. The reaction mixture was stirred without cooling for about 1 h and then quenched by the addition of $H_2O$ (500 mL). The solution was extracted with EtOAc (300 mL) then dried with anhydrous sodium sulfate, filtered through Celite and concentrated. The crude solid was recrystallized from ether to afford Compound 29a (3.42 g, 58% yield) as a yellow solid, in two crops. CIMS m/e 295 ($MH^+$).

Following the general procedure of Example 29, according to Seebach, *Helv. Chimica Acta*, 1981 64: 3, benzoylcyclohexanone Compounds 29b, 29c, 29d, 29e and 29f set forth in Table 5b were prepared using appropriate reagents and starting materials.

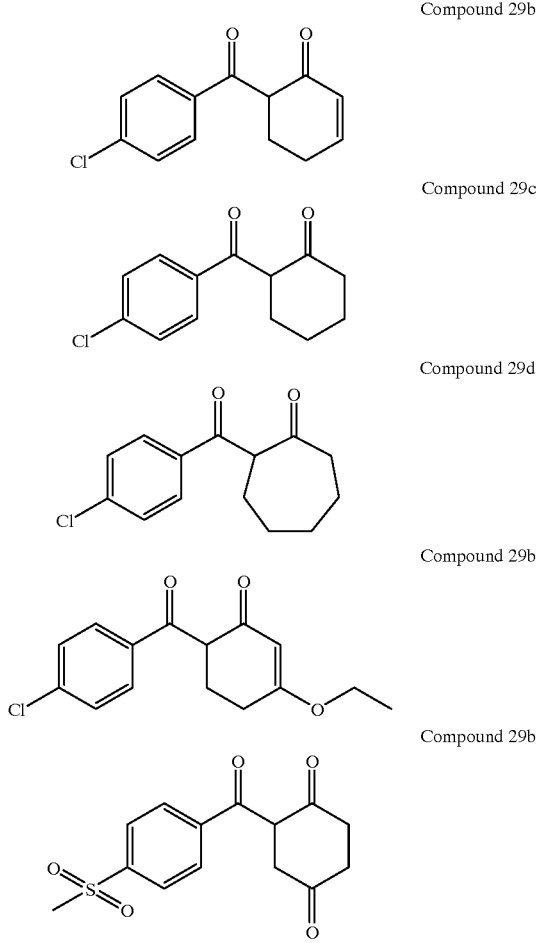

Compound 29b

Compound 29c

Compound 29d

Compound 29b

Compound 29b

EXAMPLE 30

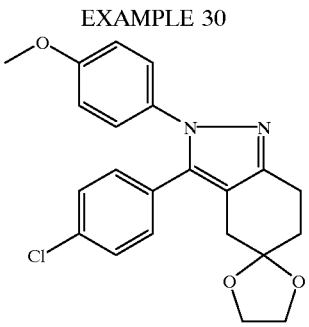

3-(4-Chlorophenyl)-2-(4-methoxyphenyl)spiro[4,5,6,7-tetrahydro-indazol-5(2H),2'-[1,3]dioxo-lane] ¼ Hydrate Compound 30a Compound 29a (1.47 g, 5.0 mMol) and 4-methoxyphenylhydrazine hydrochloride (0.87 g, 5.0 mMol) were combined in methanol (30 mL) with pyridine (1 mL). The mixture was stirred for about 4 h at about RT, then concentrated and taken up in EtOAc. The EtOAc layer was washed with $H_2O$ and dried over anhydrous sodium sulfate, then filtered through Celite and concentrated to afford Compound 30a (1.30 g, 66% yield) as a white solid (Rf=0.48). CIMS m/e 397 (MH+).

Following the general procedure of Example 30, Compounds 30b, 30c, 30d and 30e set forth in Table 5c were prepared using appropriate reagents and starting materials:

TABLE 5c

| Ex# | Formula | $R_1$ | $R_2$ | $Z_5$ | $Z_6$ | $Z_7$ |
|---|---|---|---|---|---|---|
| 30b | 1 | 4-F | 4-$SO_2$Me | C(O$CH_2$)$_2$ | $CH_2$ | $CH_2$ |
| 30c | 1 | 4-F | 4-OMe | C(O$CH_2$)$_2$ | $CH_2$ | $CH_2$ |
| 30d | 1 | 4-Cl | 4-$SO_2$Me | $CH_2$ | $CH_2$ | $CH_2$ |
| 30e | 2 | 4-Cl | 4-$SO_2$Me | $CH_2$ | $CH_2$ | $CH_2$ |

EXAMPLE 31

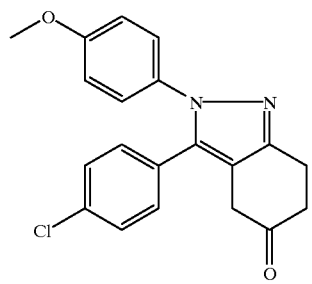

3-(4-Chlorophenyl)-2-(4-methoxyphenyl)-4,5,6,7-tetrahydro-2H-indazol-5-one

Compound 31

Compound 30 (2.0 g) and 37% HCl (11 mL) were combined in a 50 mL round bottom flask and stirred for about 1 h under nitrogen, then quenched with water (100 mL) and extracted with ether (2×50 mL). The ether layer was dried over anhydrous sodium sulfate, filtered through Celite and concentrated in ether with iodine visualization to afford Compound 31 (1.2 g, 68% yield) as a white solid. CIMS m/e 368 (MH+).

EXAMPLE 32

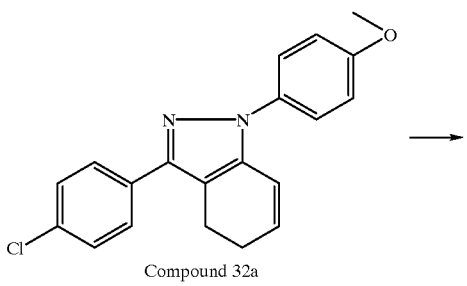

Compound 32a

59
-continued

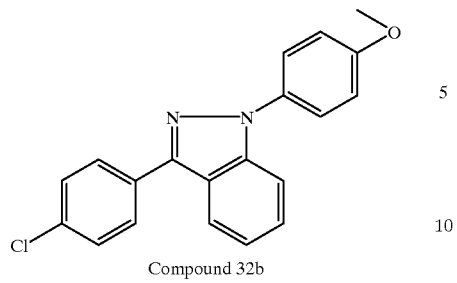

Compound 32b 3-(4-Chlorophenyl)-1-(4-methoxyphenyl)-1H-indazole 0.25 Hydrate

Compound 32b

Compound 32a was dissolved in dichloromethane and treated with 3 to 4 equivalents of DDQ. The reaction was followed by TLC and concentrated when completed (from about 24 h to about 48 h at about RT). The crude product was purified by column chromatography to afford Compound 32b (78% yield). CIMS m/e 335 (MH$^+$).

Following the general procedure of Example 32, compounds of the invention wherein $Z_5$ is $CH_2$, such as Compound 32c and Compounds 32f, 32g and 32h, were used as intermediates to prepare additional compounds of the invention wherein $Z_5$ is CH, such as Compounds 32d and 32e and Compounds 32i, 32j and 32j, as set forth in Table 5d using appropriate reagents and starting materials.

60
EXAMPLE 33

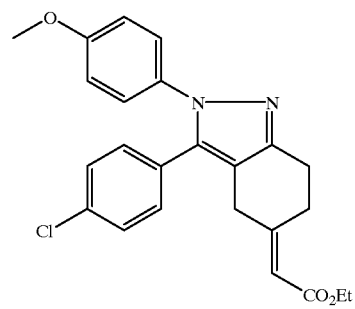

Ethyl (E) 3-(4-Chlorophenyl)-4,5,6,7-tetrahydro-2-(4-methoxyphenyl)-5-2H-indazolylideneacetate 0.35 Ethyl acetate Compound 33

Compound 28 was isolated using the procedure of Example 28 and the remaining product was purified by column chromatography to afford Compound 33 (0.55 g, 10% yield); mp: 68–70° C. CIMS m/e 423 (MH$^+$).

TABLE 5d

| Ex# | Formula | $R_1$ | $R_2$ | $Z_5$ | $Z_6$ | $Z_7$ |
|---|---|---|---|---|---|---|
| 32c | 1 | 4-CF$_3$ | 4-SO$_2$Me | CH$_2$ | HC=CH | |
| 32d | 1 | 4-Cl | 4-SO$_2$Me | CH | HC=CH | |
| 32e | 1 | 4-SO$_2$Me | 4-F | CH | HC=CH | |
| 32f | 2 | 4-Cl | 4-F | CH$_2$ | ![indole-F] | |
| 32g | 2 | 4-CF$_3$ | 4-SO$_2$Me | CH$_2$ | HC=CH | |
| 32h | 2 | 4-F | 4-SO$_2$Me | CH$_2$ | HC=CH | |
| 32i | 2 | 4-F | 4-SO$_2$Me | CH | HC=CH | |
| 32j | 2 | 4-F | 4-SO$_2$Me | CH | COEt | CH |
| 32k | 2 | 4-Cl | 4-F | CH | ![indole-F] | |

EXAMPLE 34

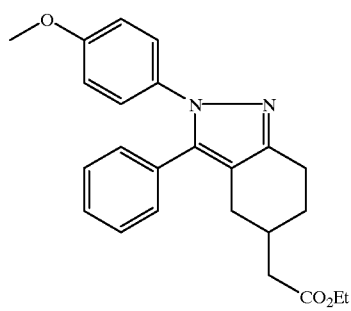

Ethyl 4,5,6,7-Tetrahydro-2-(4-methoxyphenyl)-3-phenyl-2H-indazol-5-acetate 0.30 Diethyl ether Compound 34

The ester Compound 33 (0.92 g, 2.2 mMol) and ammonium formate (1.42 g, 22 mMol) were dissolved in EtOH (20 mL), then 10% Pd/C (0.24 g) was added. The reaction mixture was stirred overnight, then filtered through a pad of Celite, concentrated and dissolved in ether. The ether solution was washed with water, then dried over anhydrous sodium sulfate, filtered and concentrated to afford Compound 34 (0.72 g, 85% yield) as a light yellow oil. CIMS m/e 391 (MH$^+$).

EXAMPLE 35

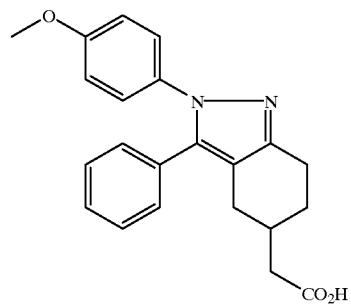

2-(4-Methoxyphenyl)-3-phenyl-4,5,6,7-tetrahydro-2H-indazol-5-acetic acid

Compound 35

The ester Compound 34 (0.36 g, 0.90 mMol) was dissolved in EtOH (5 mL) and treated with 2N NaOH (5 mL). The mixture was heated to reflux for about 0.5 h and treated after cooling with 1N HCl (25 mL) and water (125 mL). The solution was extracted with EtOAc (3×100 mL). The extracts were dried with sodium sulfate, then filtered through Celite and concentrated to afford Compound 35 (0.30 g, 91% yield) as a white solid. CIMS m/e 363 (MH$^+$).

EXAMPLE 36

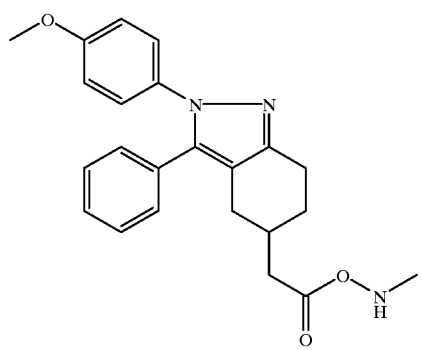

O-[2-(4-Methoxyphenyl)-3-phenyl-4,5,6,7-tetrahydro-2H-5-indazolylmethyl-carbonyl]-N-methylhydroxylamine Compound 36

The acid Compound 35 (0.50 g, 1.4 mMol) and CDI (0.23 g, 1.2 eq.) were dissolved in dichloromethane (20 mL) and then stirred for about 1 h. The mixture was treated with triethylamine (0.29 mL, 1.5 eq.) and methylhydroxylamine× HCl (0.18 g, 1.5 eq.), then stirred overnight. The reaction mixture was quenched with 0.1N HCl (100 mL) and extracted with EtOAc (3×200 mL). The extracts were dried over sodium sulfate, then filtered through Celite and concentrated to a yellow oil (0.59 g). The crude material was purified by column chromatography on silica with EtOAc to afford Compound 36 (0.26 g, 58% yield). CIMS m/e 392 (MH$^+$).

EXAMPLE 37

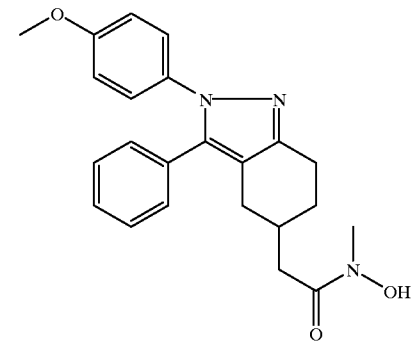

N-Hydroxy-N-methyl-2-(4-methoxyphenyl)-3-phenyl-4,5,6,7-tetrahydro-2H-indazol-5-acetamide 0.3 Ethyl acetate Compound 37

The acid Compound 35 (0.41 g, 1.1 mMol) was dissolved in dichloromethane (20 mL) at about 0° C. and treated with oxalyl chloride (0.18 mL, 2 eq.) in dichloromethane (5 mL). After about 1 h, the mixture was concentrated, taken up in dichloromethane (20 mL), and then methylhydroxylamine (0.18 g, 2.2 mMol) and triethylamine (0.31 mL, 2.2 mMol) in dichloromethane (20 mL) were added. After stirring overnight at about RT, the mixture was quenched with 0.5N HCl (100 mL) and then extracted with dichloromethane (3×100 mL). The combined extracts were dried over sodium sulfate, then filtered through a pad of Celite and concentrated to an oil. The product was purified by column chromatography on silica, eluted with EtOAc to afford Compound 37 (0.27 g, 61% yield) as a white foam. CIMS m/e 392 (MH$^+$).

EXAMPLE 38

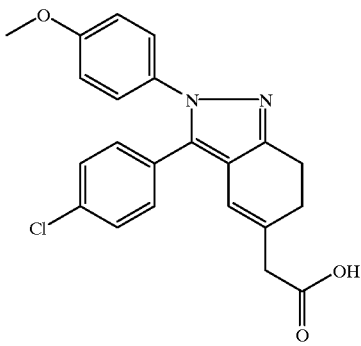

3-(4-Chlorophenyl)-6,7-dihydro-2-(4-methoxyphenyl)-2H-indazol-5-acetic acid 0.2 Ethyl acetate Compound 38

Compound 33 was treated with NaOH using the procedure of Example 35 to afford Compound 38 (89% yield) as an off-white solid. CIMS m/e 395 (MH$^+$).

EXAMPLE 39

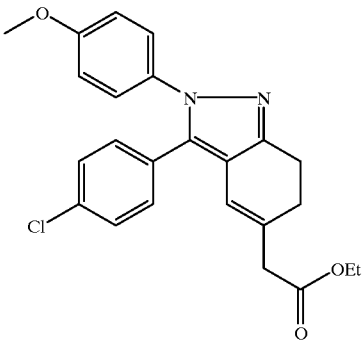

Ethyl 2-(4-methoxyphenyl)-3-(4-chlorophenyl)-6,7-dihydro-2H-indazol-5-acetate 0.15 Ethyl acetate Compound 39

The ester Compound 39 was prepared from the acid Compound 38 by refluxing in EtOH with a catalytic amount of concentrated sulfuric acid for about 1 h and isolated (93% yield) as an oil. CIMS m/e 423 (MH$^+$).

EXAMPLE 40

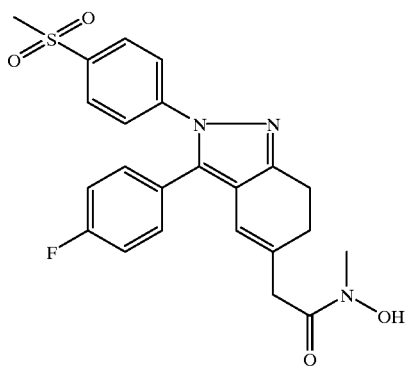

3-(4-Fluorophenyl)-6,7-dihydro-N-hydroxy-N-methyl-2-(4-methylsulfonyl phenyl)-2H-indazole-5-acetamide Compound 40

The hydroxamic acid Compound 40 was prepared (7% yield) from the carboxylic acid Compound 38 using the procedure of Example 36. CIMS m/e 456 (MH$^+$).

EXAMPLE 41

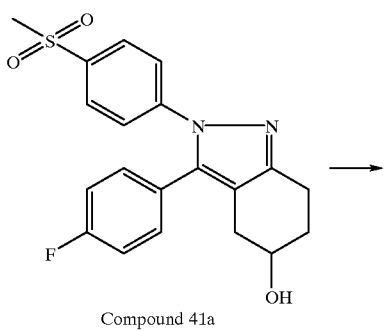

Compound 41a

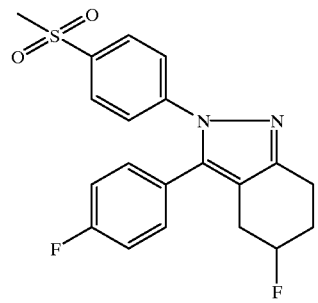

Compound 41b

3'-(4-Fluorophenyl)-2'-methylsulphonyl-5'-hydroxy-2',4',6',7'-tetrahydro-2,5'-[5H]indazole] 0.2 Hydrate Compound 41a 5-Fluoro-3-(4-fluorophenyl)-4,5,6,7-tetrahydro-2-(4-methylsulfonylphenyl)-2H-indazole Compound 41b DAST (0.020 mL, 0.16 mMol) was cooled to about −78° C. in dichloromethane (10 mL). The secondary alcohol Compound 41a prepared using the procedure in Example 19 (0.050 g, 0.13 mMol) in dichloromethane (10 mL) was added dropwise. The mixture was allowed to warm to about RT and washed with H₂O (1×50 mL). The organic layer was dried over sodium sulfate, then filtered through a pad of Celite and concentrated. The crude product was purified by column chromatography with silica gel and 2:1 hexane:ethyl acetate to afford Compound 41b (15 mg, 30% yield) as a white foam. CIMS m/e 389 (MH⁺).

EXAMPLE 42

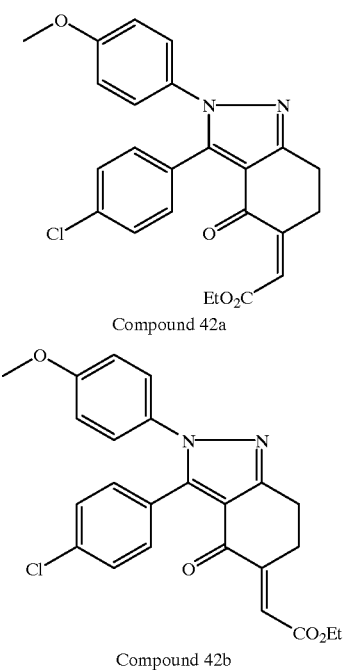

Compound 42a

Compound 42b

Ethyl (Z) 3-(4-chlorophenyl)-4,5,6,7-tetrahydro-2-(4-methoxy-phenyl)-2H-indazoliden-4-on-5-ylacetate 0.15 Ethyl acetate Compound 42a Ethyl (E) 3-(4-chlorophenyl)-4,5,6,7-tetrahydro-2-(4-methoxyphenyl)-2H-indazoliden-4-on-5-ylacetate 0.6 H₂O Compound 42b The ester Compound 39 was treated under the general conditions for reaction with DDQ (4 eq.) and refluxed overnight. Silica gel column chromatography with 2:1 hexane:ether afforded Compound 42a (43% yield) and Compound 42b (14% yield), each as an off-white solid. Compound 42a and 42b both had CIMS m/e 437 (MH⁺).

EXAMPLE 43

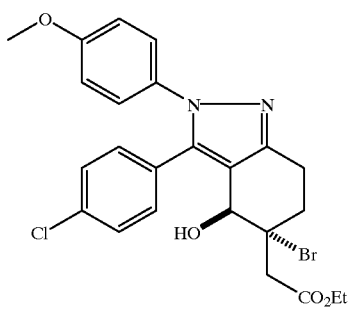

Ethyl 5(R,S)-Bromo-3-(4-chlorophenyl)-4(S,R)-hydroxy-2-(4-methoxyphenyl)-4,5,6,7-tetrahydroindazol-5-yl acetate Compound 43

The ester Compound 39 (0.10 g, 0.24 mMol) in 2 mL dichloromethane was treated at about 0° C. with 2 drops of bromine. After about 30 min, the mixture was concentrated and the residue purified by silica gel column chromatography, eluted with ether to afford Compound 43 (7 mg, 44% yield) as an off white solid. CIMS m/e 519 (MH⁺).

EXAMPLE 44

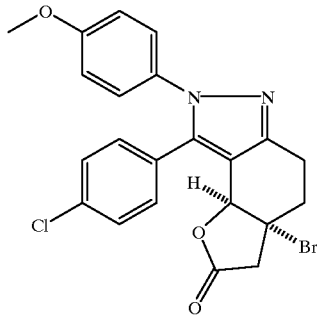

6-cis-3a-Bromo-8-(4-chlorophenyl)-3,3a,4,5,7,8b-hexahydro-7-(4-methoxyphenyl)-2H-furo[2,3-e]indazol-2-one Compound 44

The acid Compound 38 (0.50g, 1.3 mMol) was dissolved in dichloromethane and treated at about 0° C. with bromine (3 drops). After about 1 h, the mixture was concentrated and the residue was purified by silica gel column chromatography, eluted with 3:1 EtOAc:hexane to afford Compound 44 (270 mg, 45% yield) as an off white solid. CIMS m/e 474 (MH⁺).

EXAMPLE 45

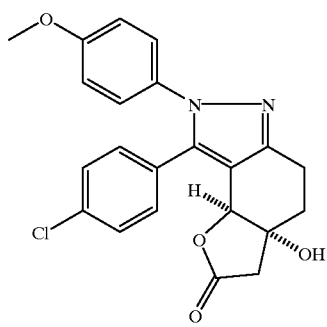

cis-8-(4-Chlorophenyl)-3,3a,4,5,7,8b-hexahydro-3a-hydroxy-7-(4-methoxyphenyl)-2H-furo[2,3-e]indazol-2-one 0.5 Hydrate Compound 45

The acid Compound 38 (0.20 g, 0.51 mMol) and MCPBA (0.17 g, 2 eq.) were combined in dichloromethane (10 mL) at about 0° C. The mixture was concentrated and the residue was purified by silica gel column chromatography, eluted with EtOAc to afford Compound 45 (70 mg, 33% yield) as an off white solid. CIMS m/e 411 (MH$^+$).

EXAMPLE 46

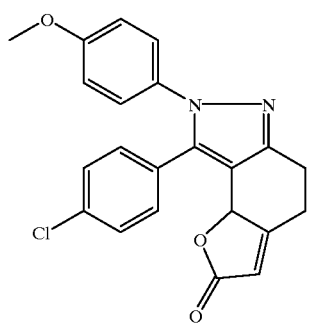

1-(4-Chlorophenyl)-2-(4-methoxyphenyl)-4,5,7,8a-tetrahydro-7H-furo[2,3-e]indazol-7-one 0.5 Ethyl acetate Compound 46

The acid Compound 38 (1.00 g, 2.53 mMol) and DDQ (1.1 g, 2 eq.) were combined in dichloromethane (20 mL) at about RT. After about 2 h, the mixture was concentrated and the residue was purified by silica gel column chromatography, eluted with EtOAc to afford Compound 46 (40 mg, 40% yield) as an off white foam. CIMS m/e 393 (MH$^+$).

EXAMPLE 47

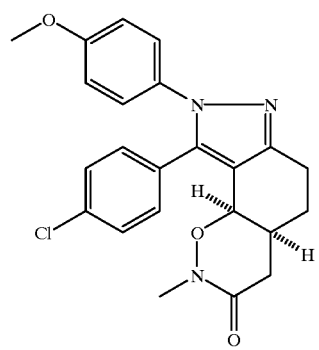

cis-9-(4-Chlorophenyl)-4,4a,5,6,8,9b-hexahydro-8-(4-methoxyphenyl)-2-methyl-2H-pyrazolo[3,4-h]-[1,2]benzoxazin-3-one 0.65 Ethyl acetate Compound 47

The acid Compound 38 was treated using the procedure of Example 37 and silica gel column chromatography, eluted with EtOAc to afford Compound 47 (40% yield). CIMS m/e 424 (MH$^+$).

EXAMPLE 48

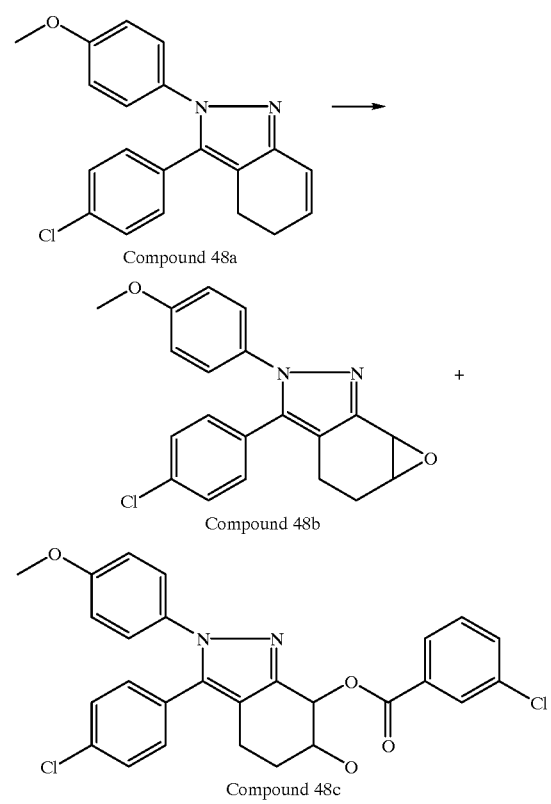

3-(4-Chlorophenyl)-2-(4-methoxyphenyl)-4,5-dihydro-2H-indazole 0.25 Hydrate

Compound 48a 3-(4-Chlorophenyl)-6,7-epoxy-4,5,6,7-tetrahydro-2-(4-methoxyphenyl)-2H-indazole 0.2 Hydrate Compound 48b 7-(3-Chlorobenzoyloxy)-3-(4-chlorophenyl)-6-hydroxy-2-(4-methoxyphenyl)-4,5,6,7-tetrahydro-2H-indazole 0.5 Hydrate Compound 48c Compound 48a made by the procedure of Example 4 (2.5 g, 7.4 mMol) (Rf=0.582) and MCPBA (2.56 g, 2 eq.) in dichloromethane were combined in a round bottom flask and stirred at about 0° C. under $N_2$. The reaction was monitored by TLC in 1:1 ethyl acetate:hexane and quenched after about 2 h with $NaHCO_3$ (ca. 100 mL) and extracted with $CH_2Cl_2$ (3×100 mL). The organic layer was dried, then filtered over Celite, concentrated and purified in 1:1 ethyl acetate:hexane by column chromatography to first afford Compound 48b (0.168 g) crystallized in $Et_2O$/hexane as an orange solid; mp: 185–188° C.; followed by Compound 48c (1.01 g, 39% yield) as a yellow-red solid (Rf=0.427).

Following the general procedure of Example 48, Compounds 48d and 48e set forth in Table 5e were prepared using appropriate reagents and starting materials.

TABLE 5E

| Ex# | Formula | $R_1$ | $R_2$ | $Z_5$ | $Z_6$ | $Z_7$ |
|-----|---------|-------|-------|-------|-------|-------|
| 48d | 1 | 4-Cl | 4-$SO_2$Me | $CH_2CH_2$ | | Epoxide |
| 48e | 1 | 4-F | 4-$SO_2$Me | $CH_2CH_2$ | | Epoxide |

EXAMPLE 49

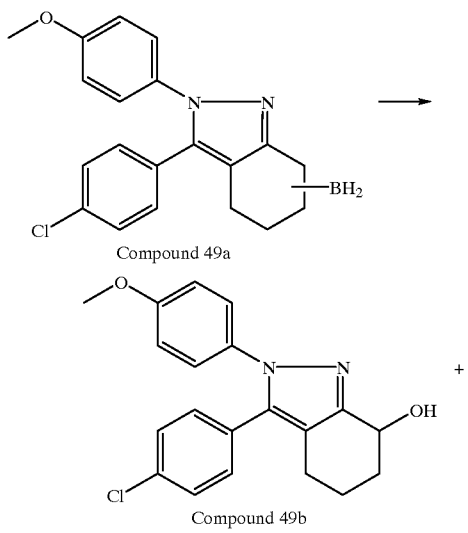

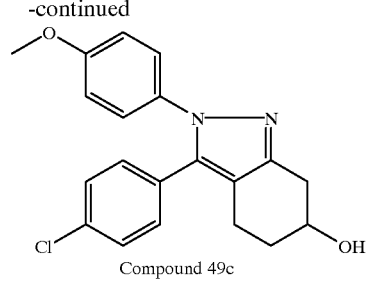

Compound 49c 3-(4-Chlorophenyl)-4,5,6,7-tetrahydro-7-hydroxy-2-(4-methoxyphenyl)-2H-indazole Compound 49b 3-(4-Chlorophenyl)-4,5,6,7-tetrahydro-6-hydroxy-2-(4-methoxyphenyl)-2H-indazole 0.20 Hydrate Compound 49c Compound 48a (0.168 g, 0.5 mMol) (Rf=0.572) and a 1.0M solution of $BH_3$ in THF (1.5 mL, 3 eq.) were combined in a round bottom flask, placed in an ice bath and stirred at about 0° C. under $N_2$. A solution of the olefin in THF was gradually added to the round bottom flask while the mixture was stirred at about 0° C. The reaction was monitored by TLC using 1:1 ethyl acetate:hexane, after about 30 min and showed two products (Rf=0.529 and 0.610). After about another 30 min, the flask was removed from the ice bath and the reaction was again examined by TLC. The mixture was stirred overnight at about RT and then concentrated. Examination by TLC showed the intermediate Compound 49a as a yellow-red solid (Rf=0.427). To a portion of this reaction mixture (5.9 mMol), 2N NaOH (18 mL, 3 eq.) was slowly added by addition funnel. Then $H_2O_2$ was slowly added and the mixture was stirred at about RT under $N_2$. The crude reaction mixture was concentrated, quenched with 600 mL $H_2O$ and extracted with EtOAc (3×300 mL). The organic layer was dried, then filtered over Celite, concentrated in 2:1 ethyl acetate:hexane and purified by column chromatography to afford Compound 49b (0.56 g, 27% yield) (Rf=0.22); mp: 174–176° C. and Compound 49c (0.080 g, 4% yield) (Rf=0.57); mp: 140–143° C.

Following the general procedure of Example 49, Compound 49d, wherein $R_2$ is 4—$SO_2$Me and $Z_6$ is CHOH, were prepared using appropriate reagents and starting materials.

EXAMPLE 50

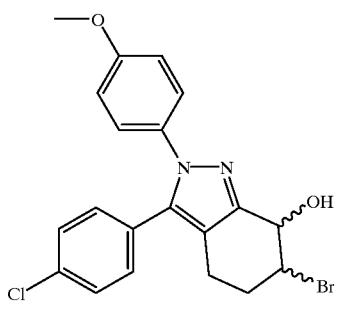

6(R,S)-Bromo-3-(4-chlorophenyl)-7(R,S)-hydroxy-
2-(4-methoxyphenyl)-4,5,6,7-tetrahydro-2H-
indazole Compound 50

To a stirred solution of Compound 48a (1.04 g, 2.97 mMol), THF (10 mL) in $H_2O$ (10 mL) at about 0° C. and NBS (0.54 g, 2.97 mMol) were added. The reaction was stirred for about 30 min, then the product was concentrated by TLC using 1:1 ethyl acetate:hexane and $H_2O$ (about 40 mL) was added. The resulting solution was placed in a separation funnel, then $H_2O$ (about 200 mL) was added and extracted using EtOAc (3×200 mL); the emulsion layer should be concentrated first. The organic layer was dried, then filtered over Celite and concentrated to afford Compound 50 (1.27 g, 97.7% yield) as a yellow or off-white solid; (Rf=0.276), mp: 183.9–185.8° C.

EXAMPLE 51

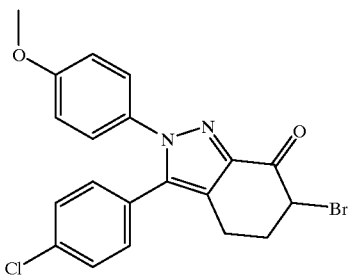

6-Bromo-3-(4-chlorophenyl)-4,5,6,7-tetrahydro-2-
(4-methoxyphenyl)-2H-indazol-7-one Compound 51

Compound 50 (0.50 g, 1.0 mMol), PCC (0.99 g, 4 eq., 4.6 mMol) and $CH_2Cl_2$ were combined in a round bottom flask, then stirred at about RT under $N_2$ and concentrated by TLC using 1:1 ethyl acetate:hexane. The reaction was filtered over paper and the round bottom flask was rinsed with EtOAc. The product was filtered over Florisil, then concentrated on a column, eluted with 1:1 ethyl acetate:hexane and crystallized in $Et_2O$/Hexane to afford Compound 51 (0.337 g, 6.8% yield) as a yellow solid; (Rf=0.50), mp: 184–186° C.

EXAMPLE 52

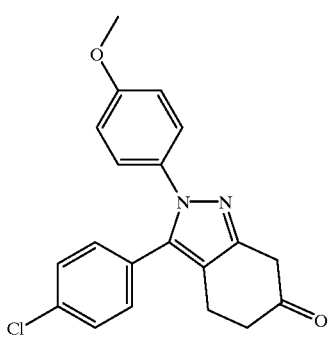

3-(4-Chlorophenyl)-4,5,6,7-tetrahydro-2-(4-
methoxyphenyl)-2H-indazole-6-one 0.2 Ethyl
acetate Compound 52a Compound 48c (0.170 g, 0.480 mMol), $BF_3Et_2O$ (1 mL) and $CH_2Cl_2$ were combined in a round bottom flask and stirred at about 0° C. under $N_2$. The reaction was monitored by TLC using EtOAc and quenched with $H_2O$ after about 1 h, then filtered over Celite and concentrated on a column, eluted with 2:1 hexane:ethyl acetate to obtain 2 products, one of which was Compound 52a (0.03 g, 18% yield) as a white solid; (Rf=0.685), mp: 167–171° C.

Following the general procedure of Example 52, Compound 52b, wherein $R_2$ is 4—$SO_2Me$, was prepared using appropriate reagents and starting materials.

EXAMPLE 53

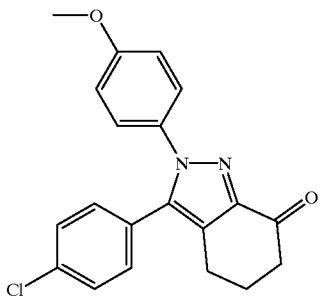

3-(4-Chlorophenyl)-4,5,6,7-tetrahydro-2-(4-
methoxyphenyl )-2H-indazole-7-one

Compound 53

Compound 49b was dissolved (0.10 g, 0.28 mMol) with acetone (20 mL) in a round bottom flask, then NMMNO (0.09 g, 3 eq.) was added, followed by the catalyst tris (triphenylphosphine)ruthenium(II)chloride [$(Ph_3P)_3RuCl_2$] (8 mg, 0.03 eq.). The reaction was monitored by TLC using 1:1 ethyl acetate:hexane and was complete after about 2.5 h. The product was filtered over a pad of silica and washed with $CH_2Cl_2$. The organic layer was then dried, filtered over Celite, concentrated and crystallized in $Et_2O$ to afford Compound 53 (0.08 g, 80% yield) (Rf=0.32), mp: 129–133° C.

We claim:
1. A compound selected from the group consisting of Formula 1 and Formula 2:

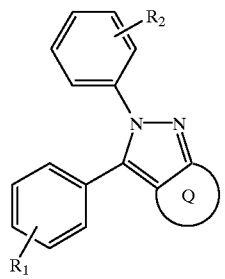

Formula 1

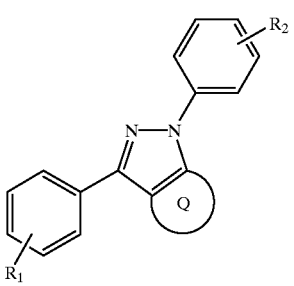

Formula 2 wherein
$R_1$ and $R_2$ are independently selected from the group consisting of hydrogen, halogen, $(C_1-C_6)$alkyl, $(C_1-C_6)$alkoxy, nitro, amino, hydroxy, trifluoro, —S$(C_1-C_6)$alkyl, —SO$(C_1-C_6)$alkyl and —SO$_2$$(C_1-C_6)$ alkyl; and
the fused moiety Q is a group selected from the group consisting of a substituted cyclohexyl or cyclohexenyl group and an optionally substituted cycloheptyl group having the formulae;

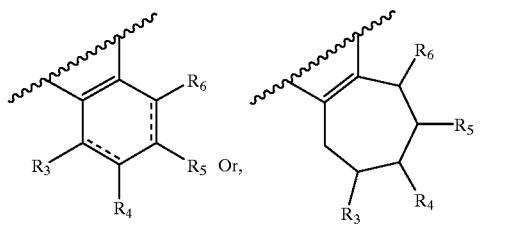

wherein
the dotted line represents a double bond at one of the two positions shown,
$R_3$ is selected from the group consisting of hydrogen, halogen, hydroxy and carbonyl;
or $R_3$ and $R_4$ taken together form a moiety selected from the group consisting of —OCOCH$_2$—, —ONH(CH$_3$)COCH$_2$—, —OCOCH= and —O—;
$R_4$ and $R_5$ are independently selected from the group consisting of hydrogen, halogen, hydroxy, carbonyl, amino, $(C_1-C_6)$alkyl, $(C_1-C_6)$alkoxy, =NOH, —NR$_7$R$_8$, —OCH$_3$, —OCH$_2$CH$_3$, —OSO$_2$NHCO$_2$CH$_3$, =CHCO$_2$CH$_2$CH$_3$, —CH$_2$CO$_2$H, —CH$_2$CO$_2$CH$_3$, —CH$_2$CO$_2$CH$_2$CH$_3$, —CH$_2$CON(CH$_3$)$_2$, —CH$_2$CO$_2$NHCH$_3$, —CHCHCO$_2$CH$_2$CH$_3$, —OCON(CH$_3$)OH, —C(COCH$_3$)$_2$, di$(C_1-C_6)$alkyl and di$(C_1-C_6)$alkoxy;

$R_6$ is selected from the group consisting of hydrogen, halogen, hydroxy, carbonyl, amino, $(C_1-C_6)$alkyl, $(C_1-C_6)$alkoxy and optionally substituted carboxyphenyl, wherein substituents on the carboxyphenyl group are selected from the group consisting of halogen, hydroxy, amino, $(C_1-C_6)$alkyl and $(C_1-C_6)$alkoxy;
or $R_5$ and $R_6$ taken together form a moiety selected from the group consisting of —O— and

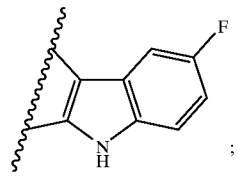

;

$R_7$ is selected from the group consisting of hydrogen, OH, —OCOCH$_3$, —COCH$_3$ and $(C_1-C_6)$alkyl; and
$R_8$ is selected from the group consisting of hydrogen, OH, —OCOCH$_3$, —COCH$_3$, $(C_1-C_6)$alkyl, —CONH$_2$ and —SO$_2$CH$_3$;
with the proviso that
if Q is a cyclohexyl group, then one of $R_3$ through $R_6$ must be a substitiuent other than hydrogen or $(C_1-C_6)$ alkyl; and
pharmaceutically acceptable salts, esters and pro-drug forms thereof.
2. The compounds according to claim 1 wherein
$R_1$ and $R_2$ are independently selected from the group consisting of hydrogen, halogen, $(C_1-C_6)$alkyl, $(C_1-C_6)$alkoxy, trifluoro, and —SO$_2(C_1-C_6)$alkyl; and
the fused moiety Q is a group selected from the group consisting of a substituted cyclohexyl and an unsubstituted cycloheptyl group wherein
$R_3$ is hydrogen;
$R_4$ and $R_5$ are independently selected from the group consisting of hydrogen, carbonyl, amino, $(C_1-C_6)$ alkoxy, —OSO$_2$NHCO$_2$CH$_3$, —CHCO$_2$CH$_2$CH$_3$, —CH$_2$CO$_2$CH$_3$, —CH$_2$CO$_2$CH$_2$CH$_3$, —CH$_2$CO$_2$NHCH$_3$ and —CHCHCO$_2$CH$_2$CH$_3$,
$R_6$ is hydrogen;
or $R_5$ and $R_6$ taken together form a moiety selected from the group consisting of —O— and

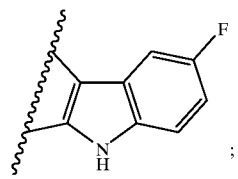

;

with the proviso that
if Q is a cyclohexyl group, then one of $R_3$ through $R_6$ must be a substituent other than hydrogen or $(C_1-C_6)$alkyl; and
pharmaceutically acceptable salts, esters and pro-drug forms thereof.
3. A pharmaceutical composition comprising a pharmaceutically acceptable carrier and a compound of claim 1.
4. A pharmaceutical composition made by mixing a compound of claim 1 and a pharmaceutically acceptable carrier.
5. A process for making a pharmaceutical composition comprising mixing a compound of claim 1 and a pharmaceutically acceptable carrier.

6. A method for alleviating a condition of inflammation in a subject in need thereof comprising administering to the subject a therapeutically effective amount of the compound of claim 1.

7. The method according to claim 6 wherein the therapeutically effective amount of the compound of claim 1 is a daily dosage of from about 10 mg to about 2000 mg.

8. The method according to claim 6 wherein the therapeutically effective amount of the compound of claim 1 is a daily dosage of from about 100 mg to about 1000 mg.

9. The method according to claim 6 wherein the condition of inflammation includes, but is not limited to, a condition caused by pain, fever or inflammation.

10. The method according to claim 6 wherein the condition caused by inflammation includes, but is not limited to, rheumatoid arthritis, osteoarthritis or degenerative joint diseases.

11. The compounds according to claim 1 wherein a compound of claim 1 in selected from the group consisting of the compounds set forth in the following Table 1:

TABLE 1

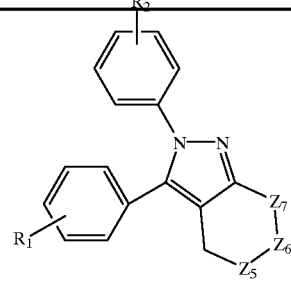

Formula 1

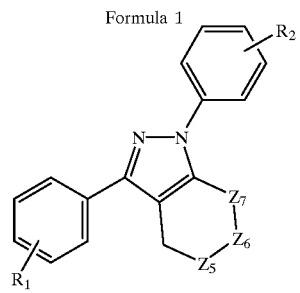

Formula 2

| Formula | $R_1$ | $R_2$ | $Z_5$ | $Z_6$ | $Z_7$ |
|---|---|---|---|---|---|
| 1 | 4-Cl | 4-SO$_2$Me | CH$_2$ | HC=CH, | |
| 1 | 4-F | 4-SO$_2$Me | CH$_2$ | HC=CH, | |
| 1 | 4-Cl | 4-SO$_2$Me | CH$_2$CH$_2$ | CH$_2$ | CH$_2$, |
| 1 | 4-Cl | 1-Me | CH$_2$CH$_2$ | CH$_2$ | CH$_2$, |
| 1 | 4-Cl | H | CH$_2$CH$_2$ | CH$_2$ | CH$_2$, |
| 1 | 4-F | 4-OMe | CH$_2$CH$_2$ | CH$_2$ | CH$_2$, |
| 1 | 4-CF$_3$ | 4-SO$_2$Me | CH$_2$ | HC=CH, | |
| 1 | 4-Cl | 4-SO$_2$Me | CH | HC=CH, | |
| 1 | 4-SO$_2$Me | F | CH | HC=CH, | |
| 1 | 4-F | 4-SO$_2$Me | CH$_2$ | Epoxide, | |
| 1 | 4-Cl | 4-SO$_2$Me | CH$_2$ | C=O | CH$_2$, |
| 2 | 4-Cl | 4-OMe | CH$_2$CH$_2$ | CH$_2$ | CH$_2$, |
| 2 | 4-F | 4-OMe | CH$_2$CH$_2$ | CH$_2$ | CH$_2$, |
| 2 | 4-Cl | 4-Me | CH$_2$CH$_2$ | CH$_2$ | CH$_2$, |
| 2 | 4-Cl | H | CH$_2$CH$_2$ | CH$_2$ | CH$_2$, |
| 2 | 4-OMe | H | CH$_2$CH$_2$ | CH$_2$ | CH$_2$, |
| 2 | 4-Cl | 4-F | CH$_2$ | 5-fluoroindol-2,3-diyl | and, |
| 2 | 4-F | 4-SO$_2$Me | CH | COEt | CH. |

12. The pharmaceutical composition according to claim 4 wherein a compound of claim 1 is selected from, the group consisting of the compounds set forth in the following Table 2:

TABLE 2

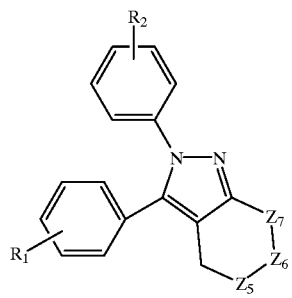

Formula 1

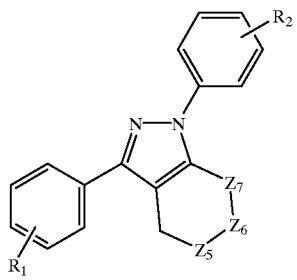

Formula 2

| Formula | $R_1$ | $R_2$ | $Z_5$ | $Z_6$ | $Z_7$ |
|---|---|---|---|---|---|
| 1 | 4-Cl | 4-SO$_2$Me | CH$_2$ | HC=CH, | |
| 1 | 4-F | 4-SO$_2$Me | CH$_2$ | HC=CH, | |
| 1 | 4-Cl | 4-SO$_2$Me | CH$_2$CH$_2$ | CH$_2$ | CH$_2$, |
| 1 | 4-Cl | 4-Me | CH$_2$CH$_2$ | CH$_2$ | CH$_2$, |
| 1 | 4-Cl | H | CH$_2$CH$_2$ | CH$_2$ | CH$_2$, |
| 1 | 4-F | 4-OMe | CH$_2$CH$_2$ | CH$_2$ | CH$_2$, |
| 1 | 4-Cl | 4-SO$_2$Me | CH$_2$ | CH$_2$ | CH$_2$, |
| 1 | 4-CF$_3$ | 4-SO$_2$Me | CH$_2$ | HC=CH, | |
| 1 | 4-Cl | 4-SO$_2$Me | CH | HC=CH, | |
| 1 | 4-SO$_2$Me | F | CH | HC=CH, | |
| 1 | 4-F | 4-SO$_2$Me | CH$_2$ | Epoxide, | |
| 1 | 4-Cl | 4-SO$_2$Me | CH$_2$ | C=O | CH$_2$, |
| 2 | 4-Cl | 4-OMe | CH$_2$CH$_2$ | CH$_2$ | CH$_2$, |
| 2 | 4-F | 4-OMe | CH$_2$CH$_2$ | CH$_2$ | CH$_2$, |
| 2 | 4-Cl | 4-Me | CH$_2$CH$_2$ | CH$_2$ | CH$_2$, |
| 2 | 4-Cl | H | CH$_2$CH$_2$ | CH$_2$ | CH$_2$, |
| 2 | 4-OMe | H | CH$_2$CH$_2$ | CH$_2$ | CH$_2$, |
| 2 | 4-Cl | 4-F | CH$_2$ | ![5-fluoroindole] | and, |
| 2 | 4-F | 4-SO$_2$Me | CH | COEt | CH. |

* * * * *